United States Patent
Serebriiskii et al.

(10) Patent No.: US 7,919,610 B2
(45) Date of Patent: Apr. 5, 2011

(54) YEAST BACTERIAL TWO-HYBRID SYSTEM AND METHODS OF USE THEREOF

(75) Inventors: Ilya G. Serebriiskii, Rockledge, PA (US); Erica A. Golemis, Oreland, PA (US); J. Keith Joung, Winchester, MA (US)

(73) Assignees: Fox Chase Cancer Center, Philadelphia, PA (US); The General Hospital Corporation, Boston, MA (US)

( * ) Notice: Subject to any disclaimer, the term of this patent is extended or adjusted under 35 U.S.C. 154(b) by 776 days.

(21) Appl. No.: 11/574,378

(22) PCT Filed: Aug. 31, 2005

(86) PCT No.: PCT/US2005/031141
§ 371 (c)(1),
(2), (4) Date: Aug. 13, 2007

(87) PCT Pub. No.: WO2006/026712
PCT Pub. Date: Mar. 9, 2006

(65) Prior Publication Data
US 2008/0118919 A1 May 22, 2008

Related U.S. Application Data

(60) Provisional application No. 60/606,266, filed on Aug. 31, 2004.

(51) Int. Cl.
*C07H 21/04* (2006.01)
*C12N 15/63* (2006.01)
*C12N 1/21* (2006.01)
*C12N 1/19* (2006.01)

(52) U.S. Cl. ............... 536/24.1; 435/320.1; 435/252.3; 435/254.2

(58) Field of Classification Search ................. None
See application file for complete search history.

(56) References Cited

OTHER PUBLICATIONS

Tolmachov, O. Designing plasmid vectors. Methods Mol Biol. 2009;542:117-29.*
Fields, et al. "A novel genetic system to detect protein-protein interactions." Nature, 340(6230): 245-246 (Jul. 20, 1989).
Joung, et al. "A bacterial two-hybrid selection system for studying protein-DNA and protein-protein interactions." Proc. Natl. Acad. Sci. USA, 97(13): 7382-7387 (Jun. 20, 2000).
Nagashima, K., et al. "Structure of the two genes coding for polypeptide chain elongation factor 1α(EF-1α) from *Saccharomyces cerevisiae*." Gene, 45: 265-273 (1986).
De Boer, H. A., et al. "The tac promoter: A functional hybrid derived from the trp and lac promoters." Proc. Natl. Acad. Sci. USA, 80: 21-25 (Jan. 1983).
Serebriiskii, I. G., et al. "Two-Hybrid System for Characterization of Protein-Protein Interactions in *E. coli*." BioTechniques, 29: 288-296 (Aug. 2000).
Serebriiskii, I. G., et al. "A Combined Yeast/Bacteria Two-hybrid System." Molecular & Cellular Proteomics, 4(6): 819-826 (Jan. 1, 2005).

* cited by examiner

*Primary Examiner* — Michele K Joike
(74) *Attorney, Agent, or Firm* — Dann, Dorfman, Herrell & Skillman; Kathleen D. Rigaut

(57) ABSTRACT

A combined yeast/bacterial two-hybrid system is disclosed.

7 Claims, 14 Drawing Sheets

Figure 1C

```
LOCUS       PGLS20 .GB    5296 BP DS-DNA    CIRCULAR   SYN         15-JAN-1998
DEFINITION  -
ACCESSION   -
KEYWORDS    -
SOURCE      -
FEATURES              Location/Qualifiers
     CDS              join(543..>1252,<1254..1256)
                      /note="cI gene [Split]"
     terminator       1336..1528
                      /note="ADH Terminator"
     rep_origin       1663..2820
                      /note="2μ origin"
     frag             3078..4280
                      /note="71 to 1273 of pFA6a-kanMX4"
     frag             3078..4280
                      /note="1 to 1203 of Kan/G418 (Bgl/Sca)-kanMX4 (C++ cut
                      with BamH1/StuI)"
     promoter         3122..3465
                      /note="TEF promoter (AG)"
     CDS              3466..4275
                      /note="Kan R gene from Tn903"
     terminator       4298..4570
                      /note="cytC terminator"
     rep_origin       4605..4874
                      /note="ColE1 ori"
     frag             1..542
                      /note="4 to 545 of TEF + UVlac promoter"
     promoter         10..422
                      /note="TEF promoter from S.cerevisiae see M15666."
     frag             467..542
                      /note="1555 to 1630 of pBT.mv"
     promoter         468..526
                      /note="lacUV5-lacO"
BASE COUNT     1414 A      1177 C      1160 G      1545 T         0 OTHER
ORIGIN      -
        1 TCATGAGGGG ATCCCCCACA CACCATAGCT TCAAAATGTT TCTACTCCTT TTTTACTCTT
       61 CCAGATTTTC TCGGACTCCG CGCATCGCCG TACCACTTCA AAACACCCAA GCACAGCATA
      121 CTAAATTTCC CCTCTTTCTT CCTCTAGGGT GTCGTTAATT ACCCGTACTA AAGGTTTGGA
      181 AAAGAAAAAA GAGACCGCCT CGTTTCTTTT TCTTCGTCGA AAAAGGCAAT AAAAATTTTT
      241 ATCACGTTTC TTTTTCTTGA AAATTTTTTT TTTGATTTTT TTCTCTTTCG ATGACCTCCC
      301 ATTGATATTT AAGTTAATAA ACGGTCTTCA ATTTCTCAAG TTTCAGTTTC ATTTTTCTTG
      361 TTCTATTACA ACTTTTTTTA CTTCTTGCTC ATTAGAAAGA AAGCATAGCA ATCTAATCTA
      421 AGGGCGGTGT TGACAATTAA TCATCGGCAT AGTATATCGG CCTAGGCTTT ACACTTTATG
      481 CTTCCGGCTC GTATAATGTG TGGAATTGTG AGCGGATAAC AATTTCACAC AGGAAACAGC
      541 GTATGAGCAC AAAAAAGAAA CCATTAACAC AAGAGCAGCT TGAGGACGCA CGTCGCCTTA
      601 AAGCAATTTA TGAAAAAAAG AAAATGAAC TTGGCTTATC CCAGGAATCT GTCGCAGACA
      661 AGATGGGGAT GGGGCAGTCA GGCGTTGGTG CTTTATTTAA TGGCATCAAT GCATTAAATG
      721 CTTATAACGC CGCATTGCTT GCAAAAATTC TCAAAGTTAG CGTTGAAGAA TTTAGCCCTT
      781 CAATCGCCAG AGAAATCTAC GAGATGTATG AAGCGGTTAG TATGCAGCCG TCACTTAGAA
      841 GTGAGTATGA GTACCCTGTT TTTTCTCATG TTCAGGCAGG GATGTTCTCA CCTGAGCTTA
      901 GAACCTTTAC CAAAGGTGAT GCGGAGAGAT GGGTAAGCAC AACCAAAAAA GCCAGTGATT
      961 CTGCATTCTG GCTTGAGGTT GAAGGTAATT CCATGACCGC ACCAACAGGC TCCAAGCCAA
     1021 GCTTTCCTGA CGGAATGTTA ATTCTCGTTG ACCCTGAGCA GGCTGTTGAG CCAGGTGATT
     1081 TCTGCATAGC CAGACTTGGG GGTGATGAGT TTACCTTCAA GAAACTGATC AGGGATAGCG
     1141 GTCAGGTGTT TTTACAACCA CTAAACCCAC AGTACCCAAT GATCCCATGC AATGAGAGTT
     1201 GTTCCGTTGT GGGGAAAGTT ATCGCTAGTC AGTGGCCTGA AGAGACGTTT GGCGAATTCA
```

Figure 1D

```
1261 AGCTTGAGCT CAGATCTCAG CTGGGCCCGG TACCGCGGCC GCTCGAGTCG ACCTGCAGCC
1321 AAGCTAATTC CGGGCGAATT TCTTATGATT TATGATTTTT ATTATTAAAT AAGTTATAAA
1381 AAAAATAAGT GTATACAAAT TTTAAAGTGA CTCTTAGGTT TTAAAACGAA AATTCTTGTT
1441 CTTGAGTAAC TCTTTCCTGT AGGTCAGGTT GCTTTCTCAG GTATAGCATG AGGTCGCTCT
1501 TATTGACCAC ACCTCTACCG GCATGCCGAG CAAATGCCTG CAAATCGCTC CCCATTTCAC
1561 CCAATTGTAG ATATGCTAAC TCCAGCAATG AGTTGATGAA TCTCGGTGTG TATTTTATGT
1621 CCTCAGAGGA CAATACCTGT TGTAATCCGT CCCAAGCTAA CGAAGCATCT GTGCTTCATT
1681 TTGTAGAACA AAAATGCAAC GCGAGAGCGC TAATTTTCA AACAAAGAAT CTGAGCTGCA
1741 TTTTTACAGA ACAGAAATGC AACGCGAAAG CGCTATTTTA CCAACGAAGA ATCTGTGCTT
1801 CATTTTTGTA AAACAAAAAT GCAACGCGAG AGCGCTAATT TTTCAAACAA AGAATCTGAG
1861 CTGCATTTTT ACAGAACAGA AATGCAACGC GAGAGCGCTA TTTTACCAAC AAAGAATCTA
1921 TACTTCTTTT TTGTTCTACA AAAATGCATC CCGAGAGCGC TATTTTCTA ACAAAGCATC
1981 TTAGATTACT TTTTTTCTCC TTTGTGCGCT CTATAATGCA GTCTCTTGAT AACTTTTGC
2041 ACTGTAGGTC CGTTAAGGTT AGAAGAAGGC TACTTTGGTG TCTATTTTCT CTTCCATAAA
2101 AAAAGCCTGA CTCCACTTCC CGCGTTTACT GATTACTAGC GAAGCTGCGG GTGCATTTTT
2161 TCAAGATAAA GGCATCCCCG ATTATATTCT ATACCGATGT GGATTGCGCA TACTTTGTGA
2221 ACAGAAAGTG ATAGCGTTGA TGATTCTTCA TTGGTCAGAA AATTATGAAC GGTTTCTTCT
2281 ATTTTGTCTC TATATACTAC GTATAGGAAA TGTTTACATT TTCGTATTGT TTTCGATTCA
2341 CTCTATGAAT AGTTCTTACT ACAATTTTTT TGTCTAAAGA GTAATACTAG AGATAAACAT
2401 AAAAAATGTA GAGGTCGAGT TTAGATGCAA GTTCAAGGAG CGAAAGGTGG ATGGGTAGGT
2461 TATATAGGGA TATAGCACAG AGATATATAG CAAAGAGATA CTTTTGAGCA ATGTTTGTGG
2521 AAGCGGTATT CGCAATATTT TAGTAGCTCG TTACAGTCCG GTGCGTTTTT GGTTTTTGA
2581 AAGTGCGTCT TCAGAGCGCT TTTGGTTTTC AAAAGCGCTC TGAAGTTCCT ATACTTTCTA
2641 GCTAGAGAAT AGGAACTTCG GAATAGGAAC TTCAAAGCGT TTCCGAAAAC GAGCGCTTCC
2701 GAAAATGCAA CGCGAGCTGC GCACATACAG CTCACTGTTC ACGTCGCACC TATATCTGCG
2761 TGTTGCCTGT ATATATATAT ACATGAGAAG AACGGCATAG TGCGTGTTTA TGCTTAAATG
2821 CGTTATGGTG CACTCTCAGT ACAATCTGCT CTGATGCCGC ATAGTTAAGC CAGCCCCGAC
2881 ACCCGCCAAC ACCCGCTGAC GCGCCCTGAC GGGCTTGTCT GCTCCCGGCA TCCGCTTACA
2941 GACAAGCTGT GACCGTCTCC GGGAGCTGCA TGTGTCAGAG GTTTTCACCG TCATCACCGA
3001 AACGCGCGAG ACGAAAGGGC CTCGTGATAC GCCTATTTTT ATAGGTTAAT GTCATGATAA
3061 TAATGGTTTC TTAGGGGGAT CTGTTTAGCT TGCCTCGTCC CCGCCGGGTC ACCCGGCCAG
3121 CGACATGGAG GCCCAGAATA CCCTCCTTGA CAGTCTTGAC GTGCGCAGCT CAGGGGCATG
3181 ATGTGACTGT CGCCCGTACA TTTAGCCCAT ACATCCCCAT GTATAATCAT TTGCATCCAT
3241 ACATTTTGAT GGCCGCACGG CGCGAAGCAA AAATTACGGC TCCTCGCTGC AGACCTGCGA
3301 GCAGGGAAAC GCTCCCCTCA CAGACGCGTT GAATTGTCCC CACGCCGCGC CCCTGTAGAG
3361 AAATATAAAA GGTTAGGATT TGCCACTGAG GTTCTTCTTT CATATACTTC CTTTTAAAAT
3421 CTTGCTAGGA TACAGTTCTC ACATCACATC CGAACATAAA CAACCATGGG TAAGGAAAAG
3481 ACTCACGTTT CGAGGCCGCG ATTAAATTCC AACATGGATG CTGATTTATA TGGGTATAAA
3541 TGGGCTCGCG ATAATGTCGG GCAATCAGGT GCGACAATCT ATCGATTGTA TGGGAAGCCC
3601 GATGCGCCAG AGTTGTTTCT GAAACATGGC AAAGGTAGCG TTGCCAATGA TGTTACAGAT
3661 GAGATGGTCA GACTAAACTG GCTGACGGAA TTTATGCCTC TTCCGACCAT CAAGCATTTT
3721 ATCCGTACTC CTGATGATGC ATGGTTACTC ACCACTGCGA TCCCCGGCAA AACAGCATTC
3781 CAGGTATTAG AAGAATATCC TGATTCAGGT GAAAATATTG TTGATGCGCT GGCAGTGTTC
3841 CTGCGCCGGT TGCATTCGAT TCCTGTTTGT AATTGTCCTT TTAACAGCGA TCGCGTATTT
3901 CGTCTCGCTC AGGCGCAATC ACGAATGAAT AACGGTTTGG TTGATGCGAG TGATTTTGAT
3961 GACGAGCGTA ATGGCTGGCC TGTTGAACAA GTCTGGAAAG AAATGCATAA GCTTTTGCCA
4021 TTCTCACCGG ATTCAGTCGT CACTCATGGT GATTTCTCAC TTGATAACCT TATTTTTGAC
4081 GAGGGGAAAT TAATAGGTTG TATTGATGTT GGACGAGTCG GAATCGCAGA CCGATACCAG
4141 GATCTTGCCA TCCTATGGAA CTGCCTCGGT GAGTTTTCTC CTTCATTACA GAAACGGCTT
4201 TTTCAAAAAT ATGGTATTGA TAATCCTGAT ATGAATAAAT TGCAGTTTCA TTTGATGCTC
4261 GATGAGTTTT TCTAATCAGT CCTCGGAGAT CCGTCCCCCT TTTCCTTTGT CGATATCATG
4321 TAATTAGTTA TGTCACGCTT ACATTCACGC CCTCCCCCCA CATCCGCTCT AACCGAAAAG
4381 GAAGGAGTTA GACAACCTGA AGTCTAGGTC CCTATTTATT TTTTTATAGT TATGTTAGTA
4441 TTAAGAACGT TATTTATATT TCAAATTTTT CTTTTTTTTC TGTACAGACG CGTGTACGCA
4501 TGTAACATTA TACTGAAAAC CTTGCTTGAG AAGGTTTTGG GACGCTCGAA GGCTTTAATT
```

Figure 1E
```
4561 TGCAAGCTGG AGACCAACAT GTGAGCAAAA GGCCAGCAAA AGGCCAGGAA CCGTAAAAAG
4621 GCCGCGTTGC TGGCGTTTTT CCATAGGCTC CGCCCCCCTG ACGAGCATCA CAAAAATCGA
4681 CGCTCAAGTC AGAGGTGGCG AAACCCGACA GGACTATAAA GATACCAGGC GTTTCCCCCT
4741 GGAAGCTCCC TCGTGCGCTC TCCTGTTCCG ACCCTGCCGC TTACCGGATA CCTGTCCGCC
4801 TTTCTCCCTT CGGGAAGCGT GGCGCTTTCT CAATGCTCAC GCTGTAGGTA TCTCAGTTCG
4861 GTGTAGGTCG TTCGCTCCAA GCTGGGCTGT GTGCACGAAC CCCCGTTCA GCCCGACCGC
4921 TGCGCCTTAT CCGGTAACTA TCGTCTTGAG TCCAACCCGG TAAGACACGA CTTATCGCCA
4981 CTGGCAGCAG CCACTGGTAA CAGGATTAGC AGAGCGAGGT ATGTAGGCGG TGCTACAGAG
5041 TTCTTGAAGT GGTGGCCTAA CTACGGCTAC .ACTAGAAGGA CAGTATTTGG TATCTGCGCT
5101 CTGCTGAAGC CAGTTACCTT CGGAAAAAGA GTTGGTAGCT CTTGATCCGG CAAACAAACC
5161 ACCGCTGGTA GCGGTGGTTT TTTTGTTTGC AAGCAGCAGA TTACGCGCAG AAAAAAAGGA
5221 TCTCAAGAAG ATCCTTTGAT CTTTTCTACG GGGTCTGACG CTCAGTGGAA CGAAAACTCA
                5281 CGTTAAGGGA TTTTGG
                      //
```

Figure 1F

```
LOCUS       PGLS20HC .   6187 BP DS-DNA    CIRCULAR    SYN         15-JAN-1998
DEFINITION  -
ACCESSION   -
KEYWORDS    -
SOURCE      -
FEATURES              Location/Qualifiers
     CDS              join(543..>1252,<1254..1256)
                      /note="cI gene [Split]"
     terminator       1336..1528
                      /note="ADH Terminator"
     rep_origin       1663..2820
                      /note="2µ origin"
     rep_origin       5496..5765
                      /note="ColE1 ori"
     frag             1..542
                      /note="4 to 545 of TEF + UVlac promoter"
     promoter         10..422
                      /note="TEF promoter"
     frag             467..542
                      /note="1555 to 1630 of pBT.mv"
     promoter         468..526
                      /note="lacUV5-lacO"
     frag             2834..5472
                      /note="1 to 2639 of Untitled1"
     frag             complement(>2834..5472)
                      /note="67 to 2706 of CamR-HIS5  cassette"
     CDS              complement(3718..4884)
                      /note="HIS5 yeast"
     promoter         complement(4885..5470)
                      /note="HIS5 prom"
     frag             complement(>2834..3710)
                      /note="95 to 1017 of CamR cassette [Split]"
     CDS              2941..3708
                      /note="CamR"
     promoter         2835..2940
                      /note="Cam R promoter"
BASE COUNT     1773 A     1297 C     1281 G     1836 T        0 OTHER
ORIGIN      -
        1 TCATGAGGGG ATCCCCCACA CACCATAGCT TCAAAATGTT TCTACTCCTT TTTTACTCTT
       61 CCAGATTTTC TCGGACTCCG CGCATCGCCG TACCACTTCA AAACACCCAA GCACAGCATA
      121 CTAAATTTCC CCTCTTTCTT CCTCTAGGGT GTCGTTAATT ACCCGTACTA AAGGTTTGGA
      181 AAAGAAAAAA GAGACCGCCT CGTTTCTTTT TCTTCGTCGA AAAAGGCAAT AAAAATTTTT
      241 ATCACGTTTC TTTTTCTTGA AAATTTTTTT TTTGATTTTT TTCTCTTTCG ATGACCTCCC
      301 ATTGATATTT AAGTTAATAA ACGGTCTTCA ATTTCTCAAG TTTCAGTTTC ATTTTTCTTG
      361 TTCTATTACA ACTTTTTTTA CTTCTTGCTC ATTAGAAAGA AAGCATAGCA ATCTAATCTA
      421 AGGGCGGTGT TGACAATTAA TCATCGGCAT AGTATATCGG CCTAGGCTTT ACACTTTATG
      481 CTTCCGGCTC GTATAATGTG TGGAATTGTG AGCGGATAAC AATTTCACAC AGGAAACAGC
      541 GTATGAGCAC AAAAAAGAAA CCATTAACAC AAGAGCAGCT TGAGGACGCA CGTCGCCTTA
      601 AAGCAATTTA TGAAAAAAAG AAAAATGAAC TTGGCTTATC CCAGGAATCT GTCGCAGACA
      661 AGATGGGGAT GGGGCAGTCA GGCGTTGGTG CTTTATTTAA TGGCATCAAT GCATTAAATG
      721 CTTATAACGC CGCATTGCTT GCAAAAATTC TCAAAGTTAG CGTTGAAGAA TTTAGCCCTT
      781 CAATCGCCAG AGAAATCTAC GAGATGTATG AAGCGGTTAG TATGCAGCCG TCACTTAGAA
      841 GTGAGTATGA GTACCCTGTT TTTTCTCATG TTCAGGCAGG GATGTTCTCA CCTGAGCTTA
      901 GAACCTTTAC CAAAGGTGAT GCGGAGAGAT GGGTAAGCAC AACCAAAAAA GCCAGTGATT
      961 CTGCATTCTG GCTTGAGGTT GAAGGTAATT CCATGACCGC ACCAACAGGC TCCAAGCCAA
     1021 GCTTTCCTGA CGGAATGTTA ATTCTCGTTG ACCCTGAGCA GGCTGTTGAG CCAGGTGATT
```

Figure 1G

```
1081 TCTGCATAGC CAGACTTGGG GGTGATGAGT TTACCTTCAA GAAACTGATC AGGGATAGCG
1141 GTCAGGTGTT TTTACAACCA CTAAACCCAC AGTACCCAAT GATCCCATGC AATGAGAGTT
1201 GTTCCGTTGT GGGGAAAGTT ATCGCTAGTC AGTGGCCTGA AGAGACGTTT GGCGAATTCA
1261 AGCTTGAGCT CAGATCTCAG CTGGGCCCGG TACCGCGGCC GCTCGAGTCG ACCTGCAGCC
1321 AAGCTAATTC CGGGCGAATT TCTTATGATT TATGATTTTT ATTATTAAAT AAGTTATAAA
1381 AAAAATAAGT GTATACAAAT TTTAAAGTGA CTCTTAGGTT TTAAAACGAA AATTCTTGTT
1441 CTTGAGTAAC TCTTTCCTGT AGGTCAGGTT GCTTTCTCAG GTATAGCATG AGGTCGCTCT
1501 TATTGACCAC ACCTCTACCG GCATGCCGAG CAAATGCCTG CAAATCGCTC CCCATTTCAC
1561 CCAATTGTAG ATATGCTAAC TCCAGCAATG AGTTGATGAA TCTCGGTGTG TATTTTATGT
1621 CCTCAGAGGA CAATACCTGT TGTAATCCGT CCCAAGCTAA CGAAGCATCT GTGCTTCATT
1681 TTGTAGAACA AAAATGCAAC GCGAGAGCGC TAATTTTTCA AACAAAGAAT CTGAGCTGCA
1741 TTTTTACAGA ACAGAAATGC AACGCGAAAG CGCTATTTTA CCAACGAAGA ATCTGTGCTT
1801 CATTTTGTA AAACAAAAAT GCAACGCGAG AGCGCTAATT TTTCAAACAA GAATCTGAG
1861 CTGCATTTTT ACAGAACAGA ATGCAACGC GAGAGCGCTA TTTTACCAAC AAAGAATCTA
1921 TACTTCTTTT TTGTTCTACA AAAATGCATC CCGAGAGCGC TATTTTCTA ACAAAGCATC
1981 TTAGATTACT TTTTTCTCC TTTGTGCGCT CTATAATGCA GTCTCTTGAT AACTTTTGC
2041 ACTGTAGGTC CGTTAAGGTT AGAAGAAGGC TACTTTGGTG TCTATTTTCT CTTCCATAAA
2101 AAAAGCCTGA CTCCACTTCC CGCGTTTACT GATTACTAGC GAAGCTGCGG GTGCATTTTT
2161 TCAAGATAAA GGCATCCCCG ATTATATTCT ATACCGATGT GGATTGCGCA TACTTTGTGA
2221 ACAGAAAGTG ATAGCGTTGA TGATTCTTCA TTGGTCAGAA AATTATGAAC GGTTTCTTCT
2281 ATTTTGTCTC TATATACTAC GTATAGGAAA TGTTTACATT TTCGTATTGT TTCGATTCA
2341 CTCTATGAAT AGTTCTTACT ACAATTTTTT TGTCTAAAGA GTAATACTAG AGATAAACAT
2401 AAAAAATGTA GAGGTCGAGT TTAGATGCAA GTTCAAGGAG CGAAGGTGG ATGGGTAGGT
2461 TATATAGGGA TATAGCACAG AGATATATAG CAAAGAGATA CTTTTGAGCA ATGTTTGTGG
2521 AAGCGGTATT CGCAATATTT TAGTAGCTCG TTACAGTCCG GTGCGTTTTT GGTTTTTTGA
2581 AAGTGCGTCT TCAGAGCGCT TTTGGTTTTC AAAAGCGCTC TGAAGTTCCT ATACTTTCTA
2641 GCTAGAGAAT AGGAACTTCG GAATAGGAAC TTCAAAGCGT TTCCGAAAAC GAGCGCTTCC
2701 GAAAATGCAA CGCGAGCTGC GCACATACAG CTCACTGTTC ACGTCGCACC TATATCTGCG
2761 TGTTGCCTGT ATATATATAT ACATGAGAAG AACGGCATAG TGCGTGTTTA TGCTTAAATG
2821 CGTTATGGTG CACTTTGCGC CGAATAAATA CCTGTGACGG AAGATCACTT CGCAGAATAA
2881 ATAAATCCTG GTGTCCCTGT TGATACCGGG AAGCCCTGGG CCAACTTTTG GCGAAAATGA
2941 GACGTTGATC GGCACGTAAG AGGTTCCAAC TTTCACCATA ATGAAATAAG ATCACTACCG
3001 GGCGTATTTT TTGAGTTATC GAGATTTTCA GGAGCTAAGG AAGCTAAAAT GGAGAAAAAA
3061 ATCACTGGAT ATACCACCGT TGATATATCC CAATGGCATC GTAAAGAACA TTTTGAGGCA
3121 TTTCAGTCAG TTGCTCAATG TACCTATAAC CAGACCGTTC AGCTGGATAT TACGGCCTTT
3181 TTAAAGACCG TAAAGAAAAA TAAGCACAAG TTTTATCCGG CCTTTATTCA CATTCTTGCC
3241 CGCCTGATGA ATGCTCATCC GGAATTCCGT ATGGCAATGA AAGACGGTGA GCTGGTGATA
3301 TGGGATAGTG TTCACCCTTG TTACACCGTT TTCCATGAGC AAACTGAAAC GTTTTCATCG
3361 CTCTGGAGTG AATACCACGA CGATTTCCGG CAGTTTCTAC ACATATATTC GCAAGATGTG
3421 GCGTGTTACG GTGAAAACCT GGCCTATTTC CCTAAAGGGT TTATTGAGAA TATGTTTTTC
3481 GTCTCAGCCA ATCCCTGGGT GAGTTTCACC AGTTTTGATT TAAACGTGGC CAATATGGAC
3541 AACTTCTTCG CCCCCGTTTT CACCATGGGC AAATATTATA CGCAAGGCGA CAAGGTGCTG
3601 ATGCCGCTGG CGATTCAGGT TCATCATGCC GTTTGTGATG GCTTCCATGT CGGCAGAATG
3661 CTTAATGAAT TACAACAGTA CTGCGATGAG TGGCAGGGCG GGCGTAAGA CGTCTATTTA
3721 TTCATTGGCC AGCTTATATA ACGTCTCCTT GAAGTACTTT ATCAAATGTG TGTTCTCCTC
3781 ATGGGTTCCA ACGGTAATTC TCAAACATCC GGAACAGCCT AATTCGTTAC CTCTAAATCT
3841 GACGACAACC CCAGATTGAG TAGCCAATTG GTAGTATAAC TTCTTTGCCA AGACATTGTC
3901 ACCCCGTTG ATCCGTATTA AAGAAAATT AGCATCTAAT CCACCAACAT ATTGGTCATC
3961 AACGTAATCC AAAGCAGTTA ATTCCTTTAA GAGGCGCATT TTCTCTTCAT TGATTATTTT
4021 CGAAGTGGCT TCCATCTTCT TTAGATTACT GTCTTGAACA GCTTTTAGTG CATATTCAGA
4081 GGCTAGGGAG GAAATATTAT AAGGCGCCTT CATTGCATTT AAAATTCTGG CCAACTCTGC
4141 TGTTGCATAT GTCATACCCA ACCTAATCCC GGCTAAACCG AATGACTTGG ATAGAGTTTG
4201 CAAAGTAACC AAGTTAGGAT ACTTGGTGAC TAGTGGAGCT GTAGAGCCAC CACAAAAATC
4261 TACGTAAGCT TCATCAACAA CGACTAACCC ATTGTCCCAA TTCTGTAAGA CCTTTTCGAT
4321 TAAACTGGTC TTAATTTTGG CTCCTGTTGG ATTACCTGGT GAAGTAACGA ACATCAACTT
4381 AATTAGCGGG TCGTTTTTCA AAATGGTTAA TACAGCTTCG GTATCCATTT GAAAAGAACC
```

Figure 1H

```
4441 GTCGGAAACA GTTAAAGGAC ATTGGACGAC TTCTATATCA TTAATGTTTG CACAAACAGA
4501 ATACATAGAA TATGTTGGTG GAAGAACCAG AATCTTTTCT TTCCCGGGAA CACAGCATGC
4561 TCTAATAATA GCATCAATAC TCTCATCAGA TCCCACACCT AGGCACAGAT TGTCAGCAGT
4621 TAAAGGTTTT ACCTCTGGGT CATTGGCATA ACTGCTTGTT TTGTTCCTGT ATTTCGTCAT
4681 TGCGGTCTTG AACTCCAATT GGTGAGGATC TGGGTAACGA TGTAAATTGG TCTTGCTCAA
4741 TTCAACTGGA GTAGGTCCAT GGGCGTTTTC ATTGGCGTCT AGCAATATAC CCTCGGTGAA
4801 ATCATCTCTT GCACAGCGAT AAGGTTCCAA GTTATAAATT TTTGGTCTAA CAATTCTTTT
4861 CAAATCAAAA ACCATAGTGT AATTTTAATA TATACGACAC ACACGTCCTG CTGGTTTATC
4921 AGGAAACAAA ATAAGAGTAG TCAATGGAAA AACTGTTTTT ACATATTAGA GGGTATATTA
4981 AACAGAACTG TGTGCATCCT TTTCAAGTTA TATAACGTGA GAGATAAAAT ATCAAGTATG
5041 TCATGTCAGG GTAAGAAACA TCAATTGAAG TGAGTCAACA GATCCAAGAA AAAAAAGCAC
5101 TAACTACGTC ACTACACCAT GAACTATTGA AAATTGGTAG TTTAGTCATC TCAGATTCCA
5161 TTCATTGGAA AAAACAATTG ATTCATAACA ATTAACTTCG GATTAGTCAT TAATTATTTC
5221 AATGCTTGAC TCCTTTTTGA ATAGTATCAC CCGGATCGTG GTCACATGAT CAAATAAATT
5281 ATTGCATTAC CAATGGCTTC TGTATTAGTT ACTCTCCAGG AAATGTCTCA ACATAACCGG
5341 TCACCATATT TATGATAACA ATTTTTAACC ATTTACCCTT TATTTTGCA AAGTTATGAC
5401 CTTTGGAATG CAGCAGAAGA AAAAAATTGA TGAAGTAGTC ATCAAACAGG TTTCGGCGAA
5461 AGACAGATCA TGTGAGCAAA AGGCCAGCAA AAGGCCAGGA ACCGTAAAAA GGCCGCGTTG
5521 CTGGCGTTTT TCCATAGGCT CCGCCCCCCT GACGAGCATC ACAAAAATCG ACGCTCAAGT
5581 CAGAGGTGGC GAAACCCGAC AGGACTATAA AGATACCAGG CGTTTCCCCC TGGAAGCTCC
5641 CTCGTGCGCT CTCCTGTTCC GACCCTGCCG CTTACCGGAT ACCTGTCCGC CTTTCTCCCT
5701 TCGGGAAGCG TGGCGCTTTC TCAATGCTCA CGCTGTAGGT ATCTCAGTTC GGTGTAGGTC
5761 GTTCGCTCCA AGCTGGGCTG TGTGCACGAA CCCCCCGTTC AGCCCGACCG CTGCGCCTTA
5821 TCCGGTAACT ATCGTCTTGA GTCCAACCCG GTAAGACACG ACTTATCGCC ACTGGCAGCA
5881 GCCACTGGTA ACAGGATTAG CAGAGCGAGG TATGTAGGCG GTGCTACAGA GTTCTTGAAG
5941 TGGTGGCCTA ACTACGGCTA CACTAGAAGG ACAGTATTTG GTATCTGCGC TCTGCTGAAG
6001 CCAGTTACCT TCGGAAAAAG AGTTGGTAGC TCTTGATCCG GCAAACAAAC CACCGCTGGT
6061 AGCGGTGGTT TTTTGTTTG CAAGCAGCAG ATTACGCGCA GAAAAAAAGG ATCTCAAGAA
6121 GATCCTTTGA TCTTTTCTAC GGGGTCTGAC GCTCAGTGGA ACGAAAACTC ACGTTAAGGG
6181 ATTTTGG
```

FIGURE 1I

```
LOCUS       PBR_UV5_AL    4320 BP  DS-DNA    CIRCULAR   SYN         18-DEC-2002
DEFINITION  -
ACCESSION   -
KEYWORDS    -
 BASE COUNT      1088 A       1061 C      1085 G       1086 T        0 OTHER
ORIGIN      -
        1 GAATTCGAAC CCCTCCTACG ACGTCTAAGA AACCATTATT ATCATGACAT TAACCTATAA
       61 AAATAGGCGT ATCACGAGGC CCTTTGGATA ACCAGAAGCA ATAAAAAATC AAATCGGATT
      121 TCACTATATA ATCTCACTTT ATCTAAGATG AATCCGATGG AAGCATCCTG TTTTCTCTCA
      181 ATTTTTTTAT CTAAAACCCA GCGTTCGATG CTTCTTTGAG CGAACGATCA AAAATAAGTG
      241 CCTTCCCATC AAAAAAATAT TGACAACATA AAAACTTTG TGTTATACTT GTAACGCTAC
      301 ATGGAGATTA ACTCAATCTA GCTAGAGAGG CTTTACACTT TATGCTTCCG GCTCGTATAA
      361 TGTGTGGAAT TGTGAGCGGA TAACAATTTC ACACAGGAAA CAGCTATGAC CATGATTACG
      421 GATTCACTGG AACTCTAGAC CAAAGAGAGG ACACAATGCA GGGTTCTGTG ACAGAGTTTC
      481 TAAAACCGCG CCTGGTTGAT ATCGAGCAAG TGAGTTCGAC GCACGCCAAG GTGACCCTTG
      541 AGCCTTTAGA GCGTGGCTTT GGCCATACTC TGGGTAACGC ACTGCGCCGT ATTCTGCTCT
      601 CATCGATGCC GGGTTGCGCG GTGACCGAGG TTGAGATTGA TGGTGTACTA CATGAGTACA
      661 GCACCAAAGA AGGCGTTCAG GAAGATATCC TGGAAATCCT GCTCAACCTG AAAGGGCTGG
      721 CGGTGAGAGT TCAGGGCAAA GATGAAGTTA TTCTTACCTT GAATAAATCT GGCATTGGCC
      781 CTGTGACTGC AGCCGATATC ACCCACGACG GTGATGTCGA ATCGTCAAG CCGCAGCACG
      841 TGATCTGCCA CCTGACCGAT GAGAACGCGT CTATTAGCAT GCGTATCAAA GTTCAGCGCG
      901 GTCGTGGTTA TGTGCCGGCT TCTACCCGAA TTCATTCGGA AGAAGATGAG CGCCCAATCG
      961 GCCGTCTGCT GGTCGACGCA TGCTACAGCC CTGTGGAGCG TATTGCCTAC AATGTTGAAG
     1021 CAGCGCGTGT AGAACAGCGT ACCGACCTGG ACAAGCTGGT CATCGAAATG GAAACCAACG
     1081 GCACAATCGA TCCTGAAGAG GCGATTCGTC GTGCGGCAAC CATTCTGGCT GAACAACTGG
     1141 AAGCTTTCGT TGACTTACGT GATGTACGTC AGCCTGAAGT GAAAGAAGAG AAACCAGAGG
     1201 CGGCCGCGCA ATTGGAGCTC CTCGAGGGAT CCTAAGTAAG AAGACACAGG CGAGAGCCGC
     1261 TAGTCTAGAG ACTAGAAAAA GGCCGACAAG TCCCGCTCCG CTGAAGATCC TGGCGTAATA
     1321 GCGAAGAGGC CCGCACCGAT CGCCCTTCCC AACAGTTGCG CAGCCTGAAT GGCGAATGGG
     1381 ACGCGCCCTG TAGCGGCGCA TTAAGCGCGG CGGGTGTGG GGTTACGCGC AGCGTGACCG
     1441 CTACACTTGC CAGCGCCCTA GCGCCCGCTC CTTTCGCTTT CTTCCCTTCC TTTCTCGCCA
     1501 CGTTCGCCGG CTTTCCCCGT CAAGCTCTAA ATCGGGGGCT CCCTTTAGGG TTCCGATTTA
     1561 GTGCTTTACG GCACCTCGAC CCCAAAAAAC TTGATTAGGG TGATGGTTCA CGTAGTGGGC
     1621 CATCGCCCTG ATAGACGGTT TTTCGCCCTT TGACGTTGGA GTCCACGTTC TTTAATAGTG
     1681 GACTCTTGTT CCAAACTGGA ACAACACTCA ACCCTATCTC GGTCTATTCT TTTGATTTAT
     1741 AAGGGATTTT GCCGATTTCG GCCTATTGGT TAAAAAATGA GCTGATTTAA CAAAAATTTA
     1801 ACGCGAATTT TAACAAAATA TTAACGCTTA CAATTTAGGT GGCACTTTTC GGGGAAATGT
     1861 GCGCGGAACC CCTATTGTT TATTTTTCTA AATACATTCA AATATGTATC CGCTCATGAG
     1921 ACAATAACCC TGATAAATGC TTCAATAATA TTGAAAAAGG AAGAGTATGA GTATTCAACA
     1981 TTTCCGTGTC GCCCTTATTC CCTTTTTTGC GGCATTTGC CTTCCTGTTT TTGCTCACCC
     2041 AGAAACGCTG GTGAAAGTAA AAGATGCTGA AGATCAGTTG GGTGCACGAG TGGGTTACAT
     2101 CGAACTGGAT CTCAACAGCG GTAAGATCCT TGAGAGTTTT CGCCCCGAAG AACGTTTTCC
     2161 AATGATGAGC ACTTTTAAAG TTCTGCTATG TGGCGCGGTA TTATCCCGTT TGACGCCGG
     2221 GCAAGAGCAA CTCGGTCGCC GCATACACTA TTCTCAGAAT GACTTGGTTG AGTACTCACC
     2281 AGTCACAGAA AAGCATCTTA CGGATGGCAT GACAGTAAGA GAATTATGCA GTGCTGCCAT
     2341 AACCATGAGT GATAACACTG CGGCCAACTT ACTTCTGACA ACGATCGGAG GACCGAAGGA
     2401 GCTAACCGCT TTTTTGCACA ACATGGGGGA TCATGTAACT CGCCTTGATC GTTGGGAACC
     2461 GGAGCTGAAT GAAGCCATAC CAAACGACGA GCGTGACACC ACGATGCCTG CAGCAATGGC
     2521 AACAACGTTG CGCAAACTAT TAACTGGCGA ACTACTTACT CTAGCTTCCC GGCAACAATT
     2581 AATAGACTGG ATGGAGGCGG ATAAAGTTGC AGGACCACTT CTGCGCTCGG CCCTTCCGGC
```

Figure 1J

```
2641 TGGCTGGTTT ATTGCTGATA AATCTGGAGC CGGTGAGCGT GGGTCTCGCG GTATCATTGC
2701 AGCACTGGGG CCAGATGGTA AGCCCTCCCG TATCGTAGTT ATCTACACGA CGGGGAGTCA
2761 GGCAACTATG GATGAACGAA ATAGACAGAT CGCTGAGATA GGTGCCTCAC TGATTAAGCA
2821 TTGGTAACTG TCAGACCAAG TTTACTCATA TATACTTTAG ATTGATTTAA AACTTCATTT
2881 TTAATTTAAA AGGATCTAGG TGAAGATCCT TTTTGATAAT CTCATGACCA AAATCCCTTA
2941 ACGTGAGTTT TCGTTCCACT GAGCGTCAGA CCCCGTAGAA AAGATCAAAG GATCTTCTTG
3001 AGATCCTTTT TTTCTGCGCG TAATCTGCTG CTTGCAAACA AAAAAACCAC CGCTACCAGC
3061 GGTGGTTTGT TTGCCGGATC AAGAGCTACC AACTCTTTTT CCGAAGGTAA CTGGCTTCAG
3121 CAGAGCGCAG ATACCAAATA CTGTCCTTCT AGTGTAGCCG TAGTTAGGCC ACCACTTCAA
3181 GAACTCTGTA GCACCGCCTA CATACCTCGC TCTGCTAATC CTGTTACCAG TGGCTGCTGC
3241 CAGTGGCGAT AAGTCGTGTC TTACCGGGTT GGACTCAAGA CGATAGTTAC CGGATAAGGC
3301 GCAGCGGTCG GGCTGAACGG GGGGTTCGTG CACACAGCCC AGCTTGGAGC GAACGACCTA
3361 CACCGAACTG AGATACCTAC AGCGTGAGCT ATGAGAAAGC GCCACGCTTC CCGAAGGGAG
3421 AAAGGCGGAC AGGTATCCGG TAAGCGGCAG GGTCGGAACA GGAGAGCGCA CGAGGGAGCT
3481 TCCAGGGGGA AACGCCTGGT ATCTTTATAG TCCTGTCGGG TTTCGCCACC TCTGACTTGA
3541 GCGTCGATTT TTGTGATGCT CGTCAGGGGG GCGGAGCCTA TGGAAAAACG CCAGCAACGC
3601 GGCCTTTTTA CGGTTCCTGG CCTTTTGCTG GCCTTTTGCT CACATGTTCT TTCCTGCGTT
3661 ATCCCCTGAT TCTGTGGATA ACCGTATTAC CGCCTTTGAG TGAGCTGATA CCGCTCGCCG
3721 CAGCCGAACG ACCGAGCGCA GCGAGTCAGT GAGCGAGGAA GCGGAAGAGC GCCTGATGCG
3781 GTATTTTCTC CTTACGCATC TGTGCGGTAT TTCACACCGC ATATGGTGCA CTCTCAGTAC
3841 AATCTGCTCT GATGCCGCAT AGTTAAGCCA GTATACACTC CGCTATCGCT ACGTGACTGG
3901 GTCATGGCTG CGCCCCGACA CCCGCCAACA CCCGCTGACG CGCCCTGACG GGCTTGTCTG
3961 CTCCCGGCAT CCGCTTACAG ACAAGCTGTG ACCGTCTCCG GGAGCTGCAT GTGTCAGAGG
4021 TTTTCACCGT CATCACCGAA ACGCGCGAGG CAGCTGCGGT AAAGCTCATC AGCGTGGTCG
4081 TGAAGCGATT CACAGATGTC TGCCTGTTCA TCCGCGTCCA GCTCGTTGAG TTTCTCCAGA
4141 AGCGTTAATG TCTGGCTTCT GATAAAGCGG GCCATGTTAA GGGCGGTTTT TTCCTGTTTG
4201 GTCACTGATG CCTCCGTGTA AGGGGATTT CTGTTCATGG GGTAATGAT ACCGATGAAA
4261 CGAGAGAGGA TGCTCACGAT ACGGGTTACT GATGATGAAC ATGCCCGGTT ACTGGAACGG
//
```

Figure 6

A hybrid promoter element consisting of the yeast TEF promoter (yellow) and bacterial (E.coli) lacUV5 promoter (bold) (SEQ ID NO: 1)

```
TCATGAGGGGATCCCCCACACACCATAGCTTCAAAATGTTTCTACTCCTTT
TTTACTCTTCCAGATTTTCTCGGACTCCGCGCATCGCCGTACCACTTCAAA
ACACCCAAGCACAGCATACTAAATTTCCCCTCTTTCTTCCTCTAGGGTGTC
GTTAATTACCCGTACTAAAGGTTTGGAAAAGAAAAAGAGACCGCCTCGT
TTCTTTTTCTTCGTCGAAAAAGGCAATAAAAATTTTTATCACGTTTCTTTTT
CTTGAAAATTTTTTTTTTGATTTTTTTCTCTTTCGATGACCTCCCATTGATAT
TTAAGTTAATAAACGGTCTTCAATTTCTCAAGTTTCAGTTTCATTTTTCTTG
TTCTATTACAACTTTTTTTACTTCTTGCTCATTAGAAAGAAAGCATAGCAA
TCTAATCTAAGGGCGGTGTTGACAATTAATCATCGGCATAGTATATCGGCC
TAGGCTTTACACTTTATGCTTCCGGCTCGTATAATGTGTGGAATTGTG
AGCGGATAACAATTTCACACAGGAAACAGCGT
```

YEAST BACTERIAL TWO-HYBRID SYSTEM AND METHODS OF USE THEREOF

This application is a 35 U.S.C. §371 application which claims priority to PCT/US05/31141 filed Aug. 31, 2005 which in turn claims priority to U.S. Provisional Application 60/606,266 filed Aug. 31, 2004, the disclosure of each of these applications being incorporated herein by reference.

This application claims priority to U.S. Provisional Application 60/606,266 filed Aug. 31, 2004, the entire disclosure of which is incorporated herein by reference.

Pursuant to 35 U.S.C. §202(c) it is acknowledged that the U.S. Government has certain rights in the invention described herein, which was made in part with funds from the National Institutes of Health, Grant Numbers RO1CA63366 and K08 DK02883.

FIELD OF THE INVENTION

This invention relates to the field of molecular biology. More specifically, the invention provides novel compositions and methods to facilitate the isolation and characterization of novel, protein-protein interactions involved in the regulation of cell growth and metabolism.

BACKGROUND OF THE INVENTION

Several publications and patent documents are cited throughout this application to better define the state of the art to which this invention pertains. Each of the foregoing citations is incorporated by reference herein.

Yeast two-hybrid systems (Chien et al. 1991; Fields and Song 1989; Gyuris et al. 1993; Vojtek et al. 1993) are standard tools used to identify novel protein-protein interactions and to perform structure-function analysis on previously defined protein-protein interactions. Such systems are effective with a substantial fraction of eukaryotic proteins and have played an important role in high throughput proteomic analyses aimed at establishing sets of interacting proteins (e.g. (Giot et al. 2003; Ito et al. 2000; Li et al. 2004; Uetz et al. 2000). In order to increase the power of a two-hybrid approach to identify and analyze protein interactions in high throughput applications, one approach has been to translate the basic components of the yeast two-hybrid system to a bacterial host organism (Dove et al. 1997; Joung et al. 2000). To date, the relative effectiveness of protein interaction detection in bacterial and yeast backgrounds has not been directly compared. However, there are a number of reasons to anticipate that differences might be observed. As yeast are eukaryotes, eukaryotic proteins used as "baits" in two-hybrid screens may be more likely to be appropriately folded and post-translationally modified in yeast than in bacteria, thereby increasing their chances of identifying physiological partners. However, certain proteins can be problematic as baits in the yeast two-hybrid system; for example, proteins that are normally excluded from the nucleus in eukaryotes, that are potentially sequestered via interaction with an abundant partner evolutionarily conserved in yeast, or that stimulate transcription in yeast (i.e.—that "autoactivate"). All of these potential issues would be expected to be less problematic in the bacterial two-hybrid system. To maximize chances of obtaining all relevant interactors for a protein of interest, it would be desirable to have the capability to rapidly test a given bait in both yeast and bacterial milieus.

SUMMARY OF THE INVENTION

In accordance with the present invention, plasmids and strains suitable for use in both yeast and bacterial protein interaction systems are provided. A novel series of vectors are disclosed in which a single plasmid containing a modified promoter drives the efficient expression of a bait protein in either yeast or bacteria, thereby permitting parallel studies in both organisms. In addition, optimized supporting yeast and bacterial reporter strains are provided.

Thus, in one aspect of the invention, an isolated nucleic acid comprising a promoter sequence shown in FIG. 6 (SEQ ID NO: 1 ) which drives expression of an operably linked coding sequence in both yeast and bacteria is provided. Also provided are plasmids comprising this promoter selected from the group consisting of SEQ ID NO: 2 (pGLS20), SEQ ID NO: 3 (pGLS22) and SEQ ID NO: 4 (pGLS23) and pBR-AMP-αLPL (SEQ ID NO: 5). Host cells comprising these plasmids are also disclosed. Such host cells are preferably *E. coli* and *S. cerevisae* cells. Also disclosed are host cells selected from the group consisting of *S. cereviciae* PRT50, and diploid strains resulting from the mating of SKY191 and PRT50 strains with the appropriate partner strains.

In yet another aspect of the invention, new strains of *E. coli* *E. coli* KJ1567 and *E. coli* AG58A(RP28) are provided. New strains of yeast are also disclosed, e.g., *S. cerevisae* PRT50 and *S. cerevisae* PRT475.

In a preferred embodiment of the invention, a method for comparing binding interactions between a first protein and a second protein in both bacterial and yeast organismal milieus using a constructs which function in both organisms, comprising a) providing yeast and bacterial host cells, each comprising,
 i) a reporter gene operably linked to a DNA sequence comprising a protein binding site;
 ii) a first fusion gene which expresses a first fusion protein, said first fusion protein comprising said first protein covalently bonding to a binding moiety which is capable of specifically binding to said protein binding site which is driven by a the promoter element as claimed in claim 1 and
 iii) a second fusion gene which expresses a second fusion protein, said second fusion protein comprising said second protein covalently bonded to gene activating moiety;
b) allowing said first and second proteins to interact; and
c) measuring expression of said reporter gene as a measure of said interaction between said first and second proteins in both *E. coli* and yeast.

Also provided in the present invention are kits for practicing the method described above. An exemplary kit comprises
a) a plasmid selected from the group consisting of (SEQ ID NO: 2 (pGLS20), SEQ ID NO: 3 (pGLS22) and SEQ ID NO: 4 (pGLS23);
b) at least one of pAC-AMP-αLPL, and/or pBR-AMP-αLPL;
c) an *E. coli* strain selected from the group consisting of *E. coli* KJ1567 or *E. coli* AG58A(RP28); and
d) a yeast strain selected from the group consisting of PRT50 and PRT475.

BRIEF DESCRIPTION OF THE DRAWINGS

FIG. 6. The hybrid promoter sequence of SEQ ID NO: 1.

DETAILED DESCRIPTION OF THE INVENTION

Figure 1:
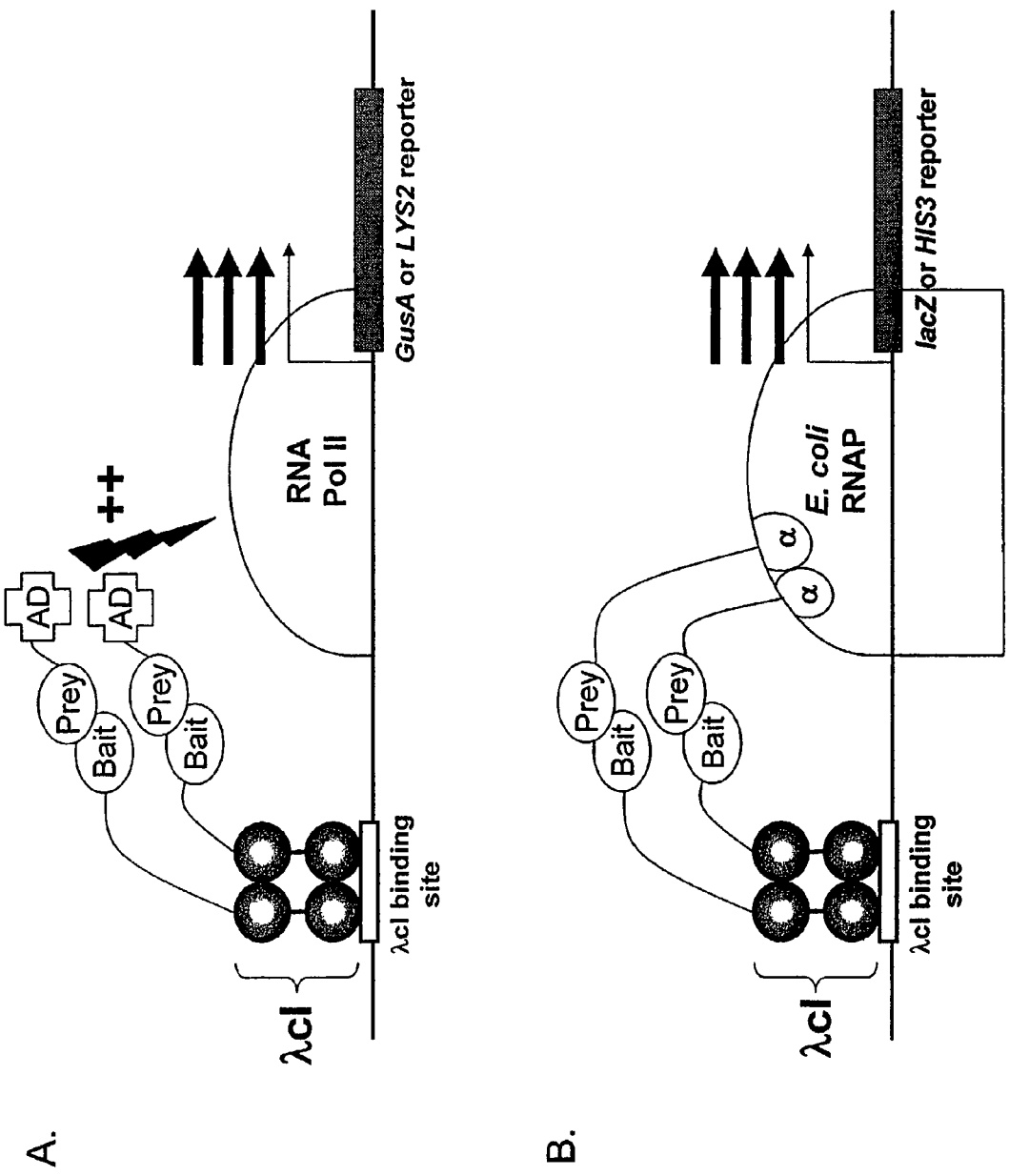
FIG. 1. Schematics of the Yeast and Bacterial two hybrid systems. A. In the yeast two-hybrid system shown, a dimeric λ cI-bait hybrid protein interacts with an activation domain (AD)-prey hybrid protein thereby stimulating transcription from an adjacent promoter that directs expression of a quantitative GusA or selectable LYS2 reporter gene. B. In the bacterial two-hybrid system shown, a dimeric λ cI-bait hybrid protein interacts with an *E. coli* RNA polymerase (RNAP) α-subunit-prey hybrid protein, thereby recruiting RNAP to an adjacent promoter that directs expression of a quantitative lacZ or selectable HIS3 reporter gene. Note that both systems utilize a λ cI-bait hybrid protein from a single plasmid effective in either organism. C-E. Sequence in pGLS20 (SEQ ID NO: 2). F-H. Sequence in pGLS22 (SEQ ID NO: 3). I-J. Sequence in pBR_AMP_alphaLP-IS-B.gb (SEQ ID NO: 5).

Two-hybrid screening is a standard methodology to identify and characterize protein-protein interactions and has become an integral component of many proteomic investigations. The two-hybrid system was initially developed using yeast as a host organism. However, bacterial two-hybrid systems have also become common laboratory tools and are preferred in some circumstances, although yeast and bacterial two-hybrid systems have never been directly compared. In accordance with the present invention, a unified yeast and bacterial two-hybrid system is provided in which a single bait expression plasmid is used in both organismal milieus. Additionally, an extensive series of leucine zipper fusion proteins of known affinities were generated to compare the efficiency of interaction detection using both systems. While both two-hybrid systems detected interactions occurring with a comparable range of interaction affinities, each demonstrated unique advantages. The yeast system produced quantitative readout over a greater dynamic range than that observed with bacteria. However, the phenomenon of "auto-activation" by baits was far less problematic in the bacterial system than in yeast. The ability to rapidly shift between yeast and bacterial systems provided by these new reagents provides a marked advantage for two-hybrid investigations. In addition, the modified expression vectors should be useful for any application requiring facile expression of a protein of interest in both yeast and bacteria. Conventional two hybrid systems have been disclosed in U.S. Pat. Nos. 5,580,736 and 6,326,150, the contents of which are incorporated herein by reference. Also provided in the present invention are kits useful for performing the methods disclosed herein.

The following definitions are provided to facilitate an understanding of the present invention.

As used herein, "reporter gene" refers to a gene whose expression may be assayed; such genes include, without limitation, LacZ, β-glucuronidase (GUS), amino acid biosynthetic genes, e.g., the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available.

A "promoter" is a DNA sequence located proximal to the start of transcription at the 5' end of an operably linked transcribed sequence. The promoter may contain one or more regulatory elements or modules which interact in modulating transcription of the operably linked gene.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

"Fusion construct" refers generally to recombinant genes which encode fusion proteins.

A "fusion protein" is a hybrid protein, i.e., a protein which has been constructed to contain domains from at least two different proteins. As used herein, a fusion protein is a hybrid protein which possesses (a) transcriptional regulatory domain from a transcriptional regulatory protein, or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, the two domains are heterologous to each other.

The transcriptional regulatory domain of the fusion protein may either activate or repress transcription of target genes, depending on the native biological activity of the domain. The bait proteins of the invention are also fusion proteins encoded by a fusion gene which comprises a protein of interest operably linked to a DNA binding moiety.

The term "fusion protein gene" refers to a DNA sequence which encodes a fusion protein. A fusion protein gene may further provide transcriptional and translational regulatory elements for the transcriptional and translational control thereof.

"Expression" is the process by which the information encoded within a gene is revealed. If the gene encodes a protein, expression involves both transcription of the DNA into mRNA, the processing of mRNA (if necessary) into a mature mRNA product, and translation of the mature mRNA into protein.

A nucleic acid molecule, such as a DNA or gene is said to be "capable of expressing" a polypeptide if the molecule contains the coding sequences for the polypeptide and the expression control sequences which, in the appropriate host environment, provide the ability to transcribe, process and translate the genetic information contained in the DNA into a protein product, and if such expression control sequences are operably-linked to the nucleotide sequence that encodes the polypeptide.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule which inserts into the host cell's chromosomal DNA in a stable manner, that is, a manner which allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle may further contain a marker suitable for use in the identification of cells transformed with the cloning vehicle. For example, "a marker gene" may be a gene which confers resistance to a specific antibiotic on a host cell.

The word "vector" is sometimes used interchangeably with "cloning vehicle".

As used herein, an "expression vehicle" is a vehicle or vector similar to the cloning vehicle but is especially designed to provide an environment which allows the expression of the cloned gene after transformation into the host. One manner of providing such an environment is to include transcriptional and translational regulatory sequences on such expression vehicle, such transcriptional and translational regulatory sequences being capable of being operably linked to the cloned gene. Another manner of providing such an environment is to provide a cloning site or sites on such vehicle, wherein a desired cloned gene and desired expression regulatory elements may be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

A "host" refers to any organism that is the recipient of a cloning or expression vehicle. In preferred embodiments, the host of the invention is a yeast cell or a cultured animal cell such as a mammalian or insect cell. In an especially preferred embodiment, the yeast host is *Saccharomyces cerevisiae*.

A "binding moiety" is a stretch of amino acids which is capable of directing specific polypeptide binding to a particular DNA sequence (i.e., a "protein binding site"). Also referred to herein as a DNA binding domain, these proteins may be homodimers or monomers that bind DNA in a sequence specific manner. Exemplary DNA binding domains of the invention include LexA, cI, glucocorticoid receptor binding domains and the Ume6 domain.

A "gene activating moiety" is a stretch of amino acids which is capable of weakly inducing the expression of a gene to whose control region it is bound. As used herein, "weakly" is meant below the level of activation effected by GAL4 activation region II (Ma and Ptashne, Cell, 48: 347, 1987) and is preferably at or below the level of activation effected by the B42 activation domain of Ma and Ptashne (Cell, 51: 413, 1987). Levels of activation may be measured using any downstream reporter gene system and comparing, in parallel assays, the level of expression stimulated by the GAL4 region II-polypeptide with the level of expression stimulated by the polypeptide to be tested.

"Purified DNA" is DNA that is not immediately contiguous with both of the coding sequences with which it is immediately contiguous (one of the 5' end and one of the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

"Substantially identical", in reference to an amino acid sequence, means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical" nucleic acid sequence codes for a substantially identical amino acid sequence as defined above.

A "transformed cell" is a yeast or bacterial cell into which (or into an ancestor of which) exogenous DNA has been introduced by means of recombinant DNA techniques.

The phrase "positioned for expression" refers to a DNA coding molecule which is positioned adjacent to a DNA sequence which directs transcription and translation of the sequence.

A "purified antibody" is an antibody at least 60 weight percent of which is free from the proteins and naturally-occurring organic molecules with which it is naturally associated. Preferably, the preparation comprises antibody in an amount of at least 75 weight percent, more preferably at least 90 weight percent, and most preferably at least 99 weight percent.

The following examples are provided to facilitate an understanding of the present invention. They are not intended to limit the invention in any way.

EXAMPLE I

The following materials and methods are provided to facilitate the practice of the present example.

Molecular and Microbiological Manipulation. Cloning of novel constructs was performed using conventional protocols. Details of the sequences and cloning sites encompassed in the plasmids described in the Results section, as well as other basic characterizations of expression properties of these plasmids, are provided hereinbelow.

Figure 4:
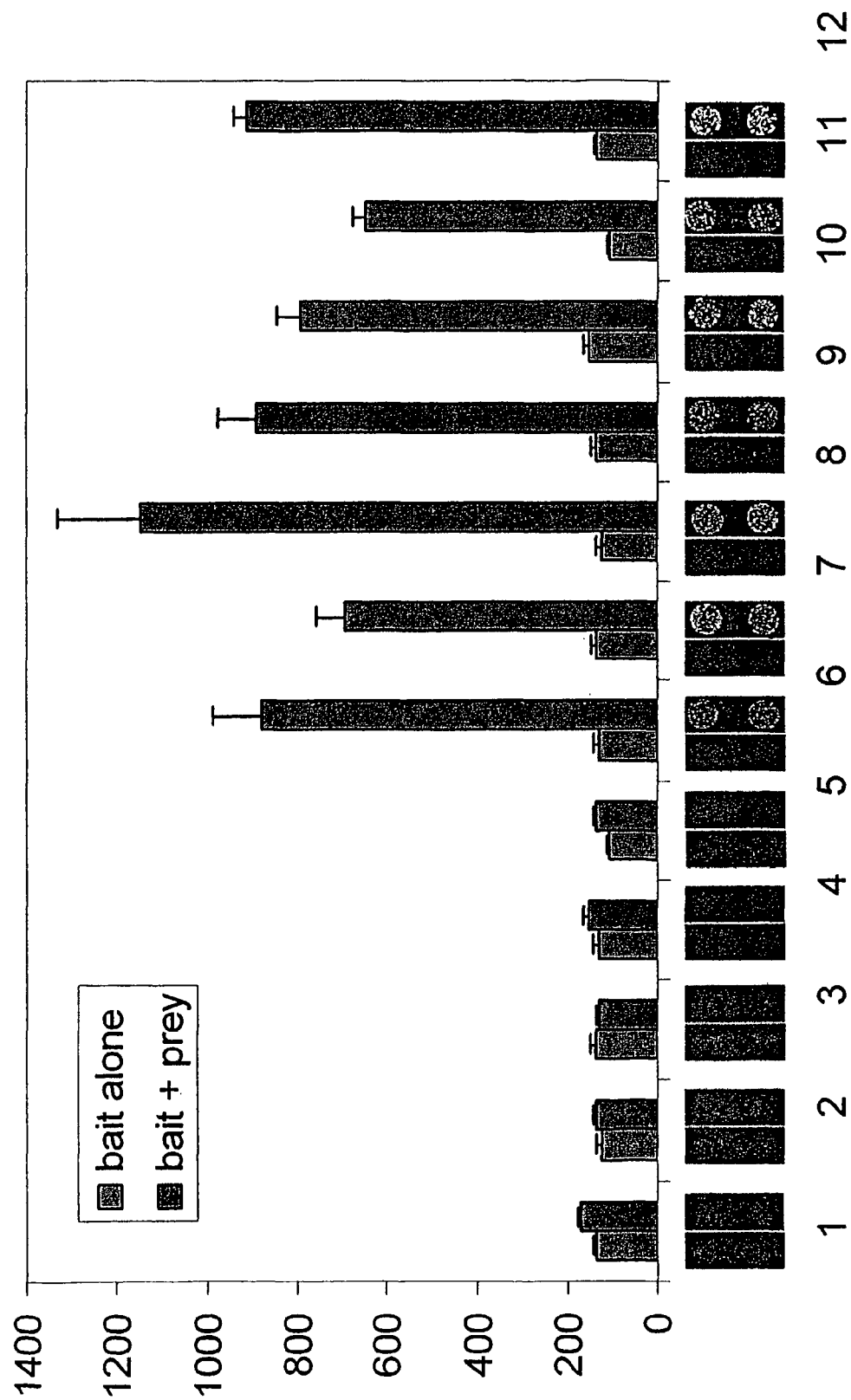
FIG. 4. Activation of colorimetric and auxotrophic reporters by zipper interaction in bacteria. Lane numbers below bar graph represent pairs of samples defined in Table 1. Bar graph reflects relative reporter activity measured by β-galactosidase assay using ONPG as a substrate. Shown below bar graph is the growth of two representative spots of colonies 24 days after plating to selective medium.
Figure 5:
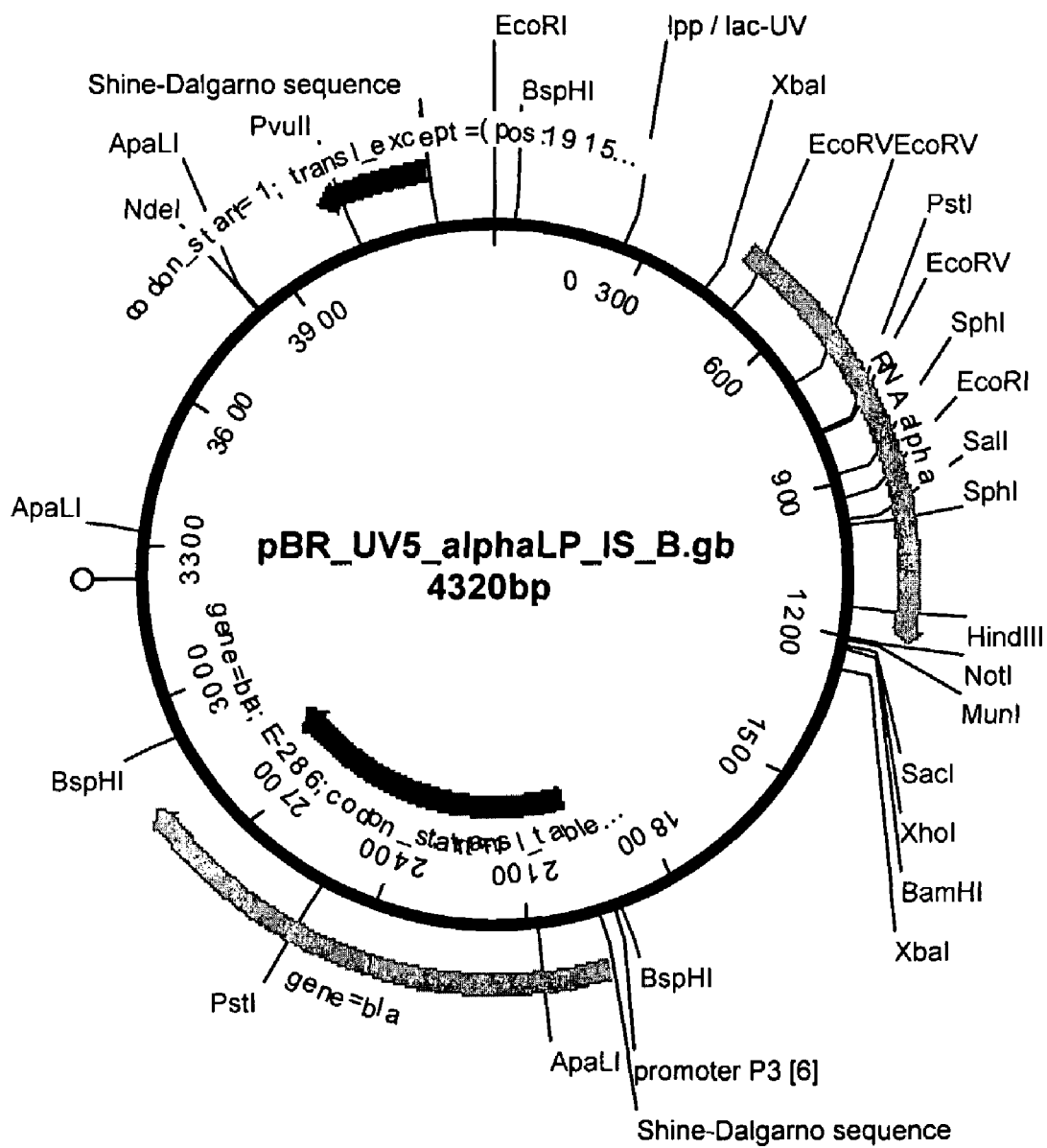
FIG. 5. Bacterial prey plasmid map of pBR_AMP_alphaL-P_IS_B.gb. This plasmid differs from pAC-AMP-αLPL in that it contains a different origin of replication, pBR as opposed to pAC.

Briefly, plasmid pGLS20 was constructed by replacing the ADH1 promoter of pGKS9 with a combination of the TEF1 promoter (from the pLexZeo plasmid, Invitrogen) and a lacUV5 promoter (from the pBT plasmid, Stratagene). To produce pGLS23, a HIS5Cm$^R$ cassette was constructed in pCR2.1 vector by combining a HIS5 cassette from pJFK (R. Hopkins, unpublished) and a CmR cassette from pMW108. This cassette was then used to replace the G418R cassette in pGLS20. Consequently, the difference between pGLS22 and pGLS23 is minor—a change in position 3267 of pGLS22 (gaattC-->gaattA) makes it pGLS23 by destroying an EcoRI site. FIG. 4 shows results using the pGLS23 (no EcoRI site) vector.

The bacterial two-hybrid prey plasmid pAC-AMP-αLPL was constructed by replacing the chloramphenicol resistance gene present in plasmid pKJ1267 (J.K.J, unpublished) with the ampicillin resistance gene from plasmid pACYC177. Leucine zipper sequences were chosen from among peptides described in (Krylov et al. 1998; Krylov et al. 1994; Moll et al. 2001): DNA was synthesized artificially to encode the described peptide sequences. To fuse the various leucine zippers to the amino-terminal domain and inter-domain linker of the E. coli RNA polymerase-α subunit, DNA fragments encoding the zipper variants were inserted into the plasmid using unique Not I and Xho I restriction sites.

Bait and prey expression. Expression of bait and prey proteins (except for bacterial RNA polymerase-α fusions, for which no antibody was available) was confirmed by Western analysis, with primary antibody to cI for baits, or hemagglutinin for preys expressed in yeast. While cI is the bait exemplified herein many different baits are known and available to the skilled artisan. To compare expression levels of cI protein in E. coli, corresponding plasmids were transformed into the DH5α strain and protein extracts prepared from exponentially growing cultures. Equal protein concentration was confirmed by Coomassie staining of a PAGE gel, then equal volumes of 1:40 (for pGLS20) or 1:100 (for pBT) dilutions of extracts in sample buffer were loaded in parallel with the same volume of undiluted extract from pGLS10-bearing cells. Proteins were resolved on a PAGE gel, and Western blot analysis was performed, using anti-cI antibodies. To compare expression levels of cI protein in yeast, corresponding plasmids were transformed in SKY191 strain and protein extracts prepared from the exponentially growing cultures. Equal protein concentration was confirmed by Coomassie staining of a PAGE gel (not shown). Then, equal volumes of extracts in sample buffer were loaded on the gel, and Western blot analysis was performed.

Reporter assays. For yeast, the activity of quantitative reporters was determined on a plate reader using a technique modified from Serebriiskii et al. 2000. Briefly, 50 µl of cultures exponentially growing in the wells of 96-well cells was added an equal volume 2×Z-buffer containing 2 mg/ml of the corresponding substrate and 50% Y-PER (Pierce), for yeast. Activity was calculated as $(OD_{420f}-OD_{420i})$ divided by $OD_{600}$, where the difference between $OD_{420i}$ and $OD_{420f}$ (initial and final readings) reflects the conversion of the colorless substrate (PNPGluc) into yellow product over a period of time from ~10-30 minutes, and $OD_{600}$ is a measure of cell density in a given sample. For each data point for each yeast experiment, activities of 5 to 8 clones were measured and averaged. All readings were taken in a plate reader; it was previously shown (Serebriiskii et al. 2000) that plate reader measurements and derivative units are proportionally correlated with the OD units taken on a spectrophotometer.

For bacterial β-galactosidase reporter gene measurements, assays were performed essentially as described (Thibodeau et al. 2004). Briefly, cultures inoculated from a fresh single colony were grown to mid-log phase and lysed by adding 1/10 volume PopCulture™ (Novagen). In a 96 well microtiter plate, 15 µl cell lysate was added to a mixture of 135 µl Z buffer and 30 µl 4 mg/ml ONPG to start the reaction. Kinetic assays were carried out by monitoring $OD_{415}$ from 0-30 minutes using a plate reader. All bacterial β-galactosidase assays were performed in triplicate.

Auxotrophic reporters were assayed as described in (Serebriiskii and Joung 2002). Bait and prey plasmids were transformed into corresponding selection strain, S. cerevisiae SKY191 or E. coli KJ1567. Growth on selection plates was measured over 5 days (yeast; note, all colonies that grew were prominent at 2 days) or 1 day (bacteria).

RESULTS

Figure 2:
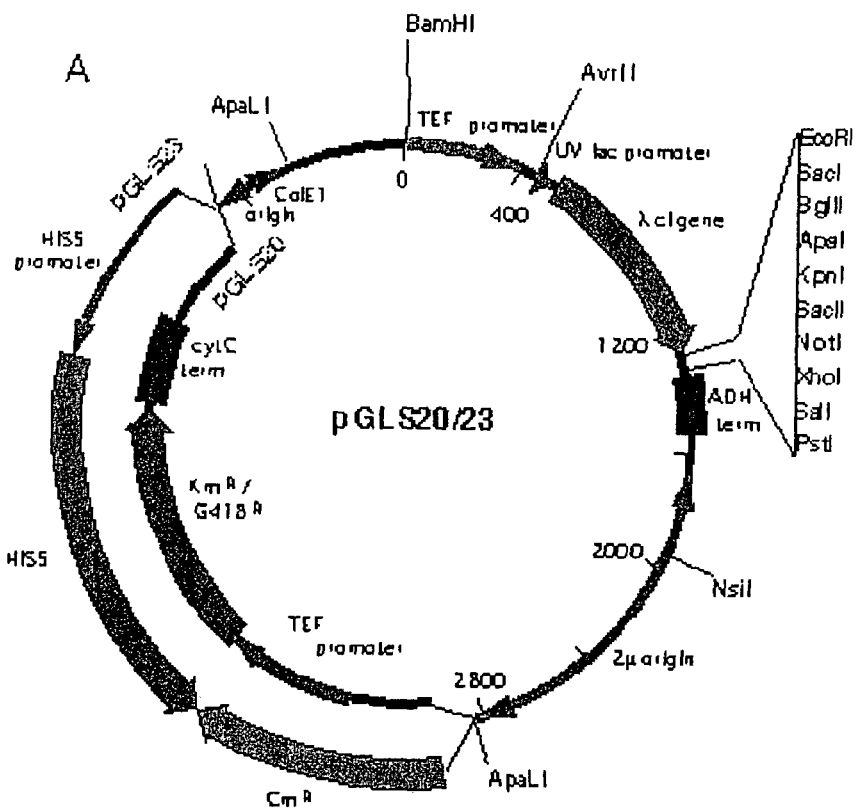
FIG. 2. Bait Expression from a combined bacteria/yeast expression plasmid. A. Plasmid pGLS20 and pGLS23 use a combined TEF1/uvLac promoter to express λ cI fused baits in yeast or bacteria. Plasmids are selected in yeast by selection for G418 resistance (pGLS20) or HIS5 complementation (pGLS23), and in bacteria by selection for Kanamycin resistance (pGLS20) or chloramphenicol resistance (pGLS23). Relative expression of cI baits from these plasmids, versus the previously described pGBS10 (yeast two-hybrid, (Serebriiskii et al. 2002)) or pBT (bacterial two-hybrid, Stratagene) vectors is shown in bacteria (center panel). B. To demonstrate relative bait levels, equal total protein concentration was confirmed by Coomassie staining of a PAGE gel loaded with equivalent amounts of cell lysate for bacteria expressing each plasmid (not shown). Then, equal volumes of 1:40 (for pGLS20) or 1:100 (for pBT) dilutions of extracts in sample buffer were loaded with the same volume of undiluted extract from pGBS10-bearing cells. Western blots using anti-cI antibodies are shown. C. pGBS10 and pGLS20 express comparable levels of λ cI baits in yeast, based on Western analysis with antibodies to λ cI. 1, 2 denotes two independent transformants in bacteria or yeast; -, denotes yeast containing no bait plasmid.
Figure 2:
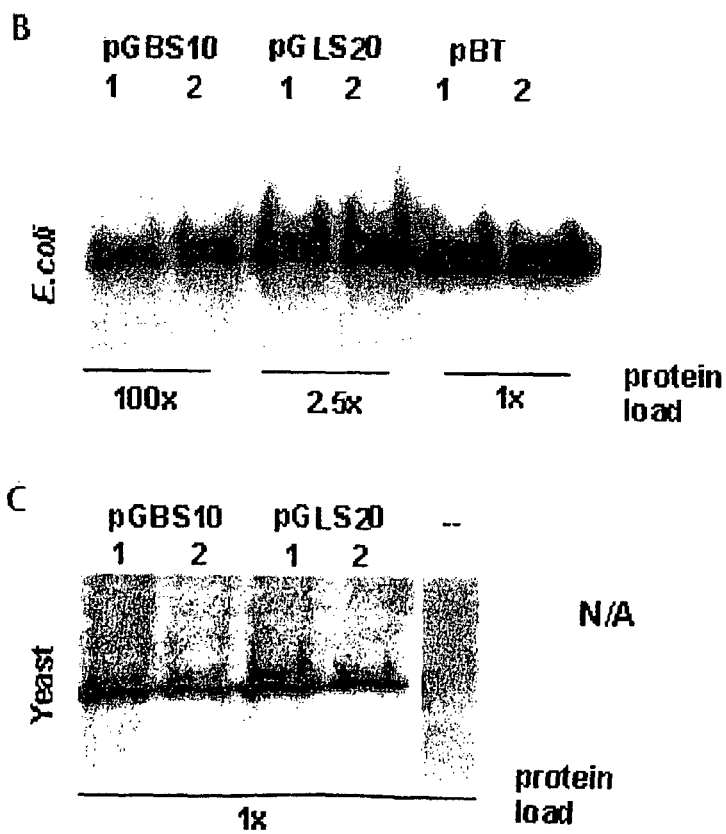

We have developed plasmids which facilitate expression and parallel screening of a single bait protein in either a yeast or bacterial two-hybrid system using a single expression plasmid (FIG. 1). As shown in FIG. 1, bait proteins are expressed as fusions to the λ cI protein in both the yeast and bacterial two-hybrid systems. To enable this, we made several modifications to the plasmid pGBS9 (Serebriiskii et al. 2002), originally developed to express bait proteins as fusions to the λ cI repressor in a yeast two-hybrid system (FIG. 2A). The ADH1 promoter from this plasmid was replaced with a tandem promoter, in which the extremely powerful TEF1 promoter (Nagashima et al. 1986) from S. cerevisiae and the E. coli lacUV5 promoter both direct expression of a λ cI coding sequence and polylinker cloning site. The resulting plasmid, pGLS20, can be maintained in yeast or bacteria based on G418 or kanamycin resistance, respectively (FIG. 2A). Other closely related plasmid derivatives (pGLS22, pGLS23) harbor the HIS5 gene to confer selection in yeast, and chloramphenicol resistance for selection in bacteria (FIG. 2A). As shown in FIG. 2B, expression of λ cI repressor using plasmid pGLS20 in bacteria is comparable to that obtained with plasmid pBT (a vector optimized for the bacterial two-hybrid system, Stratagene) and is more than 40-fold higher than that provided by the standard yeast two-hybrid expression plasmid pGBS10 (Serebriiskii et al. 2002). In yeast, expression of cI repressor fusions from pGLS20 and its derivatives is comparable to or exceeds that from pGBS10 (FIG. 2C).

We used these bi-functional pGLS plasmids to determine whether the yeast and bacterial two-hybrid systems exhibited any differences in their abilities to detect a series of interactions with differing affinities. To do this, we created a series of bait and prey fusion proteins using a set of previously characterized leucine zipper variants (Krylov et al. 1998; Krylov et al. 1994; Moll et al. 2001) with defined interaction affinities ranging from Kd>$10^{-4}$ to $10^{-15}$ M as determined in vitro (Table 1). For analysis in the bacterial two-hybrid system, plasmid pAC-AMP-αLPL (Table 2) was used to express preys from the strong inducible lpp/lacUV5 tandem promoter as fusions to the amino-terminal domain of the RNA polymerase α subunit. For the yeast two-hybrid system, pJG4-5 (Gyuris et al. 1993) was used to express preys from the inducible GAL1 promoter as fusions to the synthetic transcriptional activation domain B42 (FIG. 1). The ability of each zipper pair to activate transcription of a quantitative and an auxotrophic reporter was then assessed in bacteria and in yeast.

TABLE 1. Properties of leucine zippers used in this Example. pI calculations were made using the site at us.expasy.org/tools/pi_tool.html. Leucine zippers for many of the baits were originally described, and interaction properties characterized in vitro in (Krylov et al. 1994).

TABLE 1

Properties of leucine zippers used in this Example. pI calculations were made using the site at us.expasy.org/tools/pi_tool.html. Leucine zippers for many of the baits were originally described, and interaction properties characterized in vitro in (Krylov et al. 1994).

| Combination | Bait | pI | Prey | Kd for bait-prey (in M) |
|---|---|---|---|---|
| 1 | $EE_{12345}L$ | 4.2 | $EE_{12345}L$ | Not detectable |
| 2 | $RR_{12}EE_{345}L$ | 6.5 | $RR_{12}EE_{345}L$ | |
| 3 | $EE_{34}$ | 5.3 | $EE_{34}$ | $8.1 \times 10^{-4}$ |
| 4 | $RR_{34}$ | 10.5 | $RR_{34}$ | $3.9 \times 10^{-5}$ |
| 5 | $RR_{1234}L$ | 11.8 | $RR_{1234}L$ | $2.5 \times 10^{-7}$ |
| 6 | $RR_{34}$ | 10.5 | $EE_{34}$ | $1.0 \times 10^{-8}$ |
| 7 | $EE_{34}$ | 5.3 | $RR_{34}$ | $1.0 \times 10^{-8}$ |
| 8 | $RR_{12}EE_{345}L$ | 6.5 | $EE_{12}RR_{345}L$ | $1.3 \times 10^{-11}$ |
| 9 | $EE_{12}RR_{345}L$ | 10.4 | $RR_{12}EE_{345}L$ | $1.3 \times 10^{-11}$ |
| 10 | $RR_{12345}L$ | 12.2 | $EE_{12345}L$ | $1.1 \times 10^{-11}$ |
| 11 | $RR_{1234}L$ | 11.8 | $EE_{1234}L$ | $1.0 \times 10^{-15}$ |
| 12 | $EE_{1234}L$ | 4.3 | $RR_{1234}L$ | $1.0 \times 10^{-15}$ |

TABLE 2

Strains and plasmids used in this study.

| Plasmids | Selection in yeast/in E. coli | | Comment/description |
|---|---|---|---|
| | | | Baits |
| pGLS20* | G418$^R$ | Km$^R$ | TEF promoter ensures expression of cI in yeast, while lpp/lacUV5 promoter provides for expression in E. coli |
| pGLS22/23* | HIS5 | Cm$^R$ | Similar to pGLS20, see text for details |
| | | | Reporters |
| pRG61 pDR8 | URA3* | (Km$^R$) | λcI operators direct transcription of the gusA gene; pRG61 is less sensitive and lower background reporter than pDR8. |
| | | | Activation Domain Fusions |
| pJG4-5 | TRP1 | Ap$^R$ | GAL1 promoter provides efficient expression in yeast of a gene fused to a cassette consisting of nuclear localization sequence, transcriptional activation domain, and HA epitope tag. |
| pAC-AMP-αLPL* pBR-AMP-αLPL* | N/A N/A | Ap$^R$ Ap$^R$ | In each of the two prey plasmids, tandem lpp/lacUV5 promoters provides efficient expression in E.coli of a gene fused to E. coli RNAP alpha subunit residues 1-248. pAC-AMP-αLPL has pACYC origin of replication, while pBR-AMP-αLPL has the pBR322 origin of replication. Hence, copy numbers of the bait/prey plasmids, and therefore bait/prey expression levels can be regulated. |

| Strains | Genotype | Comment/description |
|---|---|---|
| S. cerevisiae SKY191 | MATα trp1, his3, ura3, cIop-LYS2 | Reporter strains in which the expression of the LYS2 reporter gene is directed by a weak promoter bearing a λcI DNA binding site. |
| S. cerevisiae PRT50* | MATα trp1, his3, his5, ura3, cIop-LYS2 | |
| S. cerevisiae PRT475 | MATα trp1, his3, ura3, cIop-LYS2 | Same as above |
| E. coli KJ1567* | ΔhisB463, Δ (gpt-proAB-arg-lac)XIII zaj::Tn10 [F' lacI$^q$ HIS3 aadA Kan$^R$] | Reporter strain in which the expression of the HIS3 and aadA reporter genes is directed by a weak promoter bearing a λcI DNA binding site |

TABLE 2-continued

Strains and plasmids used in this study.

| | | |
|---|---|---|
| E. coli AG58A(RP28)* | ΔhisB463, Δ (gpt-proAB-arg-lac)XIII zaj::Tn10[F' lacI$^q$ lacZ Kan$^R$] | Reporter strain in which the expression of the lacZ reporter gene is directed by a weak promo bearing a λcI DNA binding site |

*reagent produced in this study. pRG61 (Serebriiskii et al. 2002), pDR8 (Serebriiskii et al. 2002), SKY191 (Serebriiskii et al. 1999) and pJG4-5 (Gyuris et al. 1993) have been described.

Figure 3:
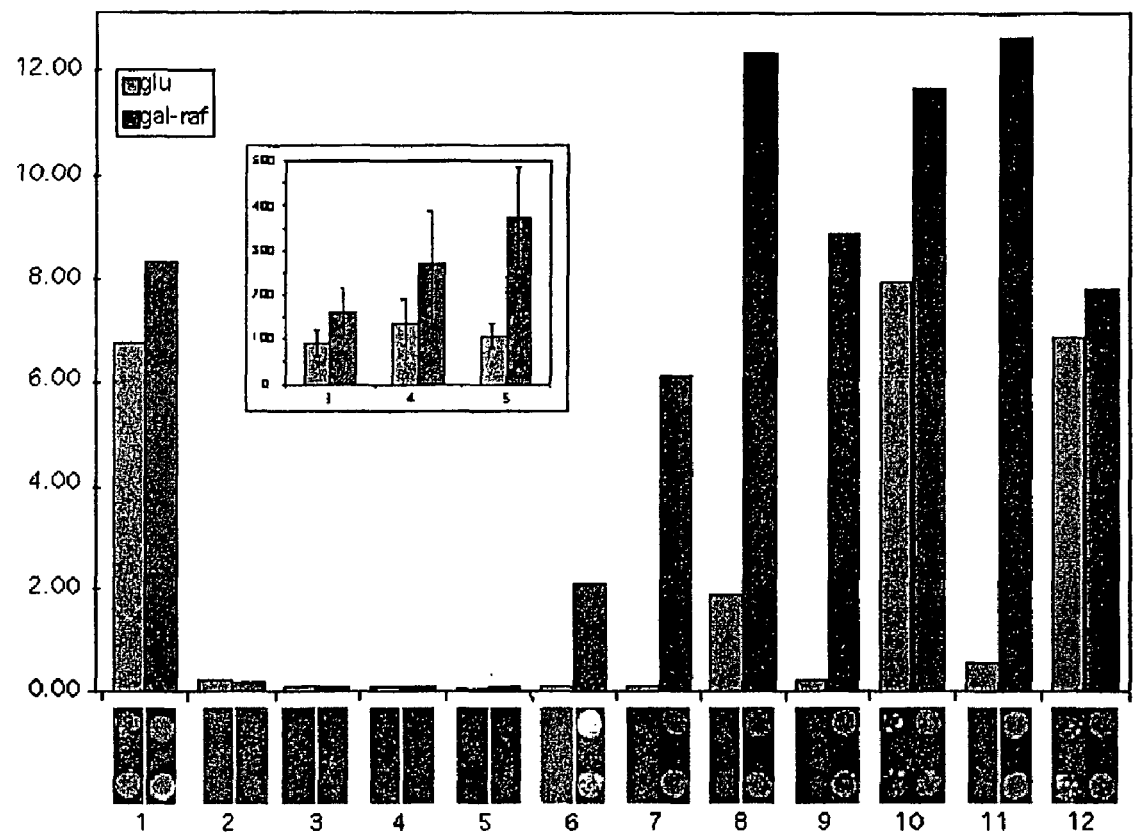
FIG. 3. Activation of colorimetric and auxotrophic reporters by zipper interaction in yeast. Lane numbers below bar graph represent pairs of samples defined in Table 1. Bar graph reflects relative reporter activity measured by beta-glucuronidase assay using PNP-gluc as a substrate. Inset, indicated samples re-analyzed using MU-gluc as a substrate. For context, values obtained for combination 6 (with a Kd of $1 \times 10^{-8}$ M), were more than 10-fold higher than those with combination 5 with the MU-gluc substrate, indicating a significant discriminating function of the yeast two-hybrid system in this affinity range (not shown). Shown below bar graph is the growth of two representative spots of colonies 2 days after plating to selective medium.

Our results in the yeast-based system demonstrate that zipper bait-prey combinations activate transcription of a quantifiable β-glucuronidase (GusA) reporter over a substantial range of affinities (FIG. 3, bar graph). In this assay, zipper pairs with reported interaction dissociation constants of $1 \times 10^{-8}$ or lower (lanes 6-12) strongly activated reporter gene expression, as detected using a colorimetric substrate (PNP-gluc). Those with Kd values of $2.5 \times 10^{-7}$ M or higher (with one exception—see below) did not strongly activate the reporter gene (FIG. 3A, lanes 1-5). β-glucuronidase activity was generally induced ~30-180 fold over baseline values with the higher affinity leucine zipper pairs. Additional testing of the lower affinity interacting pairs using a more sensitive fluorescent substrate for beta-glucuronidase, MU-gluc (FIG. 3A, inset), indicated that it was also possible to convincingly detect interactions in the range of $10^{-7}$ M, although the stimulation of GusA gene expression seen in these samples is markedly less strong than those obtained with interactions in the $10^{-8}$ M range. With the auxotrophic reporter strain (FIG. 3, panels below bar graph), cells grew under selective conditions only if the interacting zippers possessed dissociation constants of $1 \times 10^{-8}$ M or lower, paralleling the results obtained with the quantitative GusA reporter. The system did not have significant ability to discriminate interactions that interact with dissociations constants of $10^{-8}$ M or lower, suggesting the expression of the reporter gene was saturated. Importantly, for some of the baits examined, expression of the bait alone in the absence of the prey was sufficient to strongly activate transcription of the reporters, making it difficult to convincingly demonstrate protein interaction (see FIG. 3, samples 1, 10, and 12).

We next examined the abilities of the same zipper bait-prey combinations to activate transcription in the bacterial two-hybrid system (FIG. 1) using the quantifiable lacZ reporter (FIG. 4). Consistent with our results in the yeast-based system, leucine zipper pairs with reported dissociation constants lower than $10^{-8}$ M clearly stimulated expression of the lacZ reporter gene (FIG. 3, samples 6-12) whereas interaction pairs with dissociation constants $2.5 \times 10^{-7}$ M or higher failed to stimulate lacZ expression (FIG. 3, samples 1-5). We also analyzed zipper-based activation of the auxotrophic reporter HIS3 (FIG. 4, panels below bar graph). Results obtained using the auxotrophic HIS3 reporter gene closely paralleled those obtained with the lacZ reporter: only cells harboring zipper pairs with dissociation constants of $1 \times 10^{-8}$ M or lower showed growth after 24 hours on selective plates. In contrast to the results obtained in the yeast-based system, none of the baits tested exhibited autoactivation in the absence of prey partners (compare samples 1, 10 and 12 in FIGS. 3 and 4).

Our results using a closely related set of small leucine zipper bait and prey fusions suggest differential advantages for detecting protein-protein interactions in the yeast and bacterial two-hybrid systems. First, our results using quantifiable reporters suggest that the yeast-based system possesses a broader dynamic range for detecting interactions (contrast FIGS. 3 and 4). In the yeast system, interactions characterized by dissociation constants as high as $10^{-8}$ M could be detected as an increase in GusA reporter gene expression (or as high as $10^{-7}$ M if a more sensitive substrate for GusA detection was used). In contrast, in the bacterial system, only interactions characterized by dissociation constants $10^{-8}$ M or lower could be detected as an increase in lacZ expression. Second, we note that the experiments performed using bacterial two-hybrid system yield colonies on selective medium somewhat more quickly than those done in the yeast system (one day versus two). Third, our results also suggest that autoactivation by bait proteins is likely to be less problematic in bacteria than in yeast (compare lanes 1, 10, 12 in FIGS. 3 and 4). This finding is not entirely surprising given the fundamental differences in mechanisms of gene activation and the evolutionary distance between prokaryotes and eukaryotes. The lower frequency of auto-activation by baits in the bacterial two-hybrid system is a potentially significant advantage of this system compared with its yeast counterpart.

Our data also suggest that the threshold interaction strength required for robust transcriptional activation is similar in both organisms. In both the yeast and bacterial systems, full activation appears to require an interaction affinity between bait and prey fusion proteins defined by a dissociation constant in the $10^{-7}$ to $10^{-8}$ M range. Although our results demonstrate a sharp transition between no activation and full activation of the reporter genes, previous studies in both systems have demonstrated that the magnitude of transcriptional activation observed can be correlated with the affinity of the bait-prey interaction (Dove et al. 1997; Estojak et al. 1995). While we do not know the precise reason for this difference in our results compared with previous studies, we note that Estojak and coworkers assessed interactions using a series of reporters of varying stringency (i.e. containing differing numbers of binding sites for the baits) to expand the detection range: there is no technical limitation to using a similar strategy with this new system. Overall, our results strongly suggest that use of the current system as a selection tool will work best for detecting interactions with dissociation constants in the mid-to-high nanomolar range.

We note that, to our knowledge, this is the first description of a promoter combination that is potent in both yeast and bacterial milieus. In fact, we have found that our pGLS plasmids express sufficient levels of bait fusion proteins for activity in the bacterial two-hybrid system even without inducing the strong bacterial promoter. Levels of bait expression can be further regulated by the choice of prey plasmids: pBR-AMP-αLPL shares the same pBR origin of replication with the pGLS bait plasmids. Hence, by co-transformation in E. coli, the total number of copies of bait is lower, which might be advantageous if the overexpression of the bait protein is deleterious for the E. coli cell. Using pAC-AMP-αLPL, which has a different (pACYC) origin of replication, allows the full copy number of bait plasmid and therefore a potential for higher expression levels. Lastly, while this work focuses on the use of the pGLS plasmids in a two-hybrid context, we anticipate that our general promoter design might also be useful in other functional characterization studies.

REFERENCES

Chien, C. T., P. L. Bartel, R. Sternglanz, and S. Fields. 1991. The two-hybrid system: a method to identify and clone genes for proteins that interact with a protein of interest. *Proc. Nat. Acad. Sci. USA* 88: 9578-9582.

Dove, S. L., J. K. Joung, and A. Hochschild. 1997. Activation of prokaryotic transcription through arbitrary protein-protein contacts. *Nature* 386: 627-630.

Estojak, J., R. Brent, and E. A. Golemis. 1995. Correlation of two-hybrid affinity data with in vitro measurements. *Mol. Cell. Biol.* 15: 5820-5829.

Fields, S. and O. Song. 1989. A novel genetic system to detect protein-protein interaction. *Nature* 340: 245-246.

Giot, L., J. S. Bader, C. Brouwer, A. Chaudhuri, B. Kuang, Y. Li, Y. L. Hao, C. E. Ooi, B. Godwin, E. Vitols, G. Vijayadamodar, P. Pochart, H. Machineni, M. Welsh, Y. Kong, B. Zerhusen, R. Malcolm, Z. Varrone, A. Collis, M. Minto, S. Burgess, L. McDaniel, E. Stimpson, F. Spriggs, J. Williams, K. Neurath, N. Ioime, M. Agee, E. Voss, K. Furtak, R. Renzulli, N. Aanensen, S. Carrolla, E. Bickelhaupt, Y. Lazovatsky, A. DaSilva, J. Zhong, C. A. Stanyon, R. L. Finley, Jr., K. P. White, M. Braverman, T. Jarvie, S. Gold, M. Leach, J. Knight, R. A. Shimkets, M. P. McKenna, J. Chant, and J. M. Rothberg. 2003. A protein interaction map of Drosophila melanogaster. *Science* 302: 1727-1736.

Gyuris, J., E. A. Golemis, H. Chertkov, and R. Brent. 1993. Cdi1, a human G1 and S phase protein phosphatase that associates with Cdk2. *Cell* 75: 791-803.

Ito, T., K. Tashiro, S. Muta, R. Ozawa, T. Chiba, M. Nishizawa, K. Yamamoto, S. Kuhara, and Y. Sakaki. 2000. Toward a protein-protein interaction map of the budding yeast: A comprehensive system to examine two-hybrid interactions in all possible combinations between the yeast proteins. *Proc Natl Acad Sci USA* 97: 1143-1147.

Joung, J. K., E. I. Ramm, and C. O. Pabo. 2000. A bacterial two-hybrid selection system for studying protein-DNA and protein-protein interactions. *Proc Natl Acad Sci USA* 97: 7382-7387.

Krylov, D., J. Barchi, and C. Vinson. 1998. Inter-helical interactions in the leucine zipper coiled coil dimer: pH and salt dependence of coupling energy between charged amino acids. *J Mol Biol* 279: 959-972.

Krylov, D., I. Mikhailenko, and C. Vinson. 1994. A thermodynamic scale for leucine zipper stability and dimerization specificity: e and g interhelical interactions. *Embo J* 13: 2849-2861.

Li, S., C. M. Armstrong, N. Bertin, H. Ge, S. Milstein, M. Boxem, P. O. Vidalain, J. D. Han, A. Chesneau, T. Hao, D. S. Goldberg, N. Li, M. Martinez, J. F. Rual, P. Lamesch, L. Xu, M. Tewari, S. L. Wong, L. V. Zhang, G. F. Berriz, L. Jacotot, P. Vaglio, J. Reboul, T. Hirozane-Kishikawa, Q. Li, H. W. Gabel, A. Elewa, B. Baumgartner, D. J. Rose, H. Yu, S. Bosak, R. Sequerra, A. Fraser, S. E. Mango, W. M. Saxton, S. Strome, S. Van Den Heuvel, F. Piano, J. Vandenhaute, C. Sardet, M. Gerstein, L. Doucette-Stamm, K. C. Gunsalus, J. W. Harper, M. E. Cusick, F. P. Roth, D. E. Hill, and M. Vidal. 2004. A map of the interactome network of the metazoan C. elegans. *Science* 303: 540-543.

Moll, J. R., S. B. Ruvinov, I. Pastan, and C. Vinson. 2001. Designed heterodimerizing leucine zippers with a ranger of pIs and stabilities up to 10(−15) M. *Protein Sci* 10: 649-655.

Nagashima, K., M. Kasai, S. Nagata, and Y. Kaziro. 1986. Structure of the two genes coding for polypeptide chain elongation factor 1 alpha (EF-1 alpha) from *Saccharomyces cerevisiae*. *Gene* 45: 265-273.

Serebriiskii, I. and E. A. Golemis. www.fccc.edu/research/labs/golemis/InteractionTrapInWork.html.

Serebriiskii, I., V. Khazak, and E. A. Golemis. 1999. A two-hybrid dual bait system to discriminate specificity of protein interactions. *J. Biol. Chem.* 274: 17080-17087.

Serebriiskii, I. G. and J. K. Joung. 2002. Yeast and bacterial two-hybrid selection systems for studying protein-protein interactions. In *Protein-Protein Interactions: A Molecular Cloning Manual* (ed. E. Golemis), pp. 93-142. Cold Spring Harbor Laboratory Press, Cold Spring Harbor, N.Y.

Serebriiskii, I. G., 0. Mitina, E. Pugacheva, E. Benevolenskaya, E. Kotova, G. G. Toby, V. Khazak, W. G. Kaelin, J. Chernoff, and E. A. Golemis. 2002. Detection of peptides, proteins, and drugs that selectively interact with protein targets. *Genome Res.* 12: 1785-1791.

Serebriiskii, I. G., G. G. Toby, and G. E. A. 2000. Streamlined yeast colorimetric reporter assays, using scanners and plate readers. *Biotechniques* 29: 278-279, 282-274, 286-278.

Thibodeau, S. A., R. Fang, and J. K. Joung. 2004. High-throughput beta-galactosidase assay for bacterial cell-based reporter systems. *Biotechniques* 36: 410-415.

Uetz, P., L. Giot, G. Cagney, T. A. Mansfield, R. S. Judson, J. R. Knight, D. Lockshon, V. Narayan, M. Srinivasan, P. Pochart, A. Qureshi-Emili, Y. Li, B. Godwin, D. Conover, T. Kalbfleish, G. Vijayadamodar, M. Yang, M. Johnston, S. Fields, and J. M. Rothberg. 2000. A comprehensive analysis of protein-protein interactions in *Saccharomyces cerevisiae*. *Nature* 403: 623-627.

Vojtek, A. B., S. M. Hollenberg, and J. A. Cooper. 1993. Mammalian Ras interacts directly with the serine/threonine kinase Raf. *Cell* 74: 205-214.

While this invention has been disclosed with reference to specific embodiments, other embodiments and variations of this invention may be devised by those of skill in the art without departing from the true spirit and scope of the invention. The appended claims are intended to be construed to include all such embodiments and equivalent variations.

What is claimed is:

1. An isolated nucleic acid comprising a promoter sequence of SEQ ID NO: 1 which drives expression of an operably linked coding sequence in both yeast and bacteria.

2. A plasmid comprising the promoter of claim 1 selected from the group consisting of SEQ ID NO: 2 (pGLS20), SEQ ID NO: 3 (pGLS22) and SEQ ID NO: 4 (pGLS23).

3. A yeast or bacterial host cell expressing a plasmid of claim 2.

4. The host cell of claim 3 selected from the group consisting of *S. cerevisiae* SKY191, PRT50, diploid strain SKY191 and PRT50.

5. The host cell of claim 3 which is *E. coli* KJ1567 or *E. coli* AG58A(RP28).

6. A method for comparing binding interactions between a first protein and a second protein in both bacterial and yeast organismal milieus using a construct which functions in both organisms, comprising
   a) providing a yeast host cell and a bacterial host cell, each cell comprising,
      i) a reporter gene operably linked to a DNA sequence comprising a protein binding site;
      ii) a first fusion gene which expresses a first fusion protein, said first fusion protein comprising said first protein covalently bonding to a binding moiety which is capable of specifically binding to said protein binding site which is driven by the promoter sequence as claimed in claim 1 and
      iii) a second fusion gene which expresses a second fusion protein, said second fusion protein comprising said second protein covalently bonded to a gene activating moiety;
   b) allowing said first and second proteins to interact; and
   c) measuring expression of said reporter gene as a measure of said interaction between said first and second proteins in both bacteria and yeast.

7. A unified yeast and bacterial two-hybrid system for practicing the method of claim 6, comprising:
   a) a plasmid selected from the group consisting of SEQ ID NO: 2 (pGLS20), SEQ ID NO: 3 (pGLS22) and SEQ ID NO: 4 (pGLS23);
   b) at least one of pAC-AMP-αLPL and pBR-AMP-αLPL (SEQ ID NO: 5);
   c) an *E. coli* strain selected from the group consisting of *E.coli* KJ1567 and *E. coli* AG58A(RP28); and
   d) a yeast strain selected from the group consisting of PRT50, SKY191 and PRT475.

* * * * *

SEQUENCE LISTING

<160> NUMBER OF SEQ ID NOS: 5

<210> SEQ ID NO 1
<211> LENGTH: 542
<212> TYPE: DNA
<213> ORGANISM: Artificial Sequence
<220> FEATURE:
<223> OTHER INFORMATION: Synthetic Sequence

```
<400> SEQUENCE: 1
tcatgagggg atcccccaca caccatagct tcaaaatgtt tctactcctt ttttactctt      60
ccagattttc tcggactccg cgcatcgccg taccacttca aaacacccaa gcacagcata     120
ctaaatttcc cctctttctt cctctagggt gtcgttaatt acccgtacta aaggtttgga     180
aaagaaaaaa gagaccgcct cgtttctttt tcttcgtcga aaaaggcaat aaaaattttt     240
atcacgtttc tttttcttga aaatttttt tttgattttt ttctctttcg atgacctccc      300
attgatattt aagttaataa acggtcttca atttctcaag tttcagtttc attttttcttg    360 ttctattaca actttttta cttcttgctc attagaaaga aagcatagca atctaatcta      420
agggcggtgt tgacaattaa tcatcggcat agtatatcgg cctaggcttt acactttatg    480
cttccggctc gtataatgtg tggaattgtg agcggataac aatttcacac aggaaacagc    540
gt                                                                    542

<210> SEQ ID NO 2
<211> LENGTH: 5296
<212> TYPE: DNA
<213> ORGANISM: Artificial Sequence
<220> FEATURE:
<223> OTHER INFORMATION: Synthetic Sequence

<400> SEQUENCE: 2
tcatgagggg atcccccaca caccatagct tcaaaatgtt tctactcctt ttttactctt      60
ccagattttc tcggactccg cgcatcgccg taccacttca aaacacccaa gcacagcata     120
ctaaatttcc cctctttctt cctctagggt gtcgttaatt acccgtacta aaggtttgga     180
aaagaaaaaa gagaccgcct cgtttctttt tcttcgtcga aaaaggcaat aaaaattttt     240
atcacgtttc tttttcttga aaatttttt tttgattttt ttctctttcg atgacctccc      300
attgatattt aagttaataa acggtcttca atttctcaag tttcagtttc attttttcttg    360 ttctattaca actttttta cttcttgctc attagaaaga aagcatagca atctaatcta      420
agggcggtgt tgacaattaa tcatcggcat agtatatcgg cctaggcttt acactttatg    480
cttccggctc gtataatgtg tggaattgtg agcggataac aatttcacac aggaaacagc    540
gtatgagcac aaaaaagaaa ccattaacac aagagcagct tgaggacgca cgtcgcctta     600
aagcaattta tgaaaaaaag aaaaatgaac ttggcttatc ccaggaatct gtcgcagaca     660
agatggggat ggggcagtca ggcgttggtg ctttatttaa tggcatcaat gcattaaatg     720
cttataacgc cgcattgctt gcaaaaattc tcaaagttag cgttgaagaa tttagcccctt    780 caatcgccag agaaatctac gagatgtatg aagcggttag tatgcagccg tcacttagaa     840
gtgagtatga gtaccctgtt ttttctcatg ttcaggcagg gatgttctca cctgagctta     900
gaacctttac caaaggtgat gcggagagat gggtaagcac aaccaaaaaa gccagtgatt     960
ctgcattctg gcttgaggtt gaaggtaatt ccatgaccgc accaacaggc tccaagccaa    1020
gctttcctga cggaatgtta attctcgttg accctgagca ggctgttgag ccaggtgatt    1080
tctgcatagc cagacttggg ggtgatgagt ttacccttcaa gaaactgatc agggatagcg    1140
gtcaggtgtt tttacaacca ctaaacccac agtacccaat gatcccatgc aatgagagtt    1200
gttccgttgt ggggaaagtt atcgctagtc agtggcctga agagacgttt ggcgaattca    1260
agcttgagct cagatctcag ctgggcccgg taccgcggcc gctcgagtcg acctgcagcc    1320
aagctaattc cggcgaatt tcttatgatt tatgattttt attattaaat aagttataaa     1380
aaaaataagt gtatacaaat tttaaagtga ctcttaggtt ttaaaacgaa aattcttgtt    1440
```

```
cttgagtaac tctttcctgt aggtcaggtt gctttctcag gtatagcatg aggtcgctct    1500
tattgaccac acctctaccg gcatgccgag caaatgcctg caaatcgctc cccatttcac    1560
ccaattgtag atatgctaac tccagcaatg agttgatgaa tctcggtgtg tatttatgt     1620 cctcagagga caatacctgt tgtaatccgt cccaagctaa cgaagcatct gtgcttcatt    1680
ttgtagaaca aaaatgcaac gcgagagcgc taatttttca aacaaagaat ctgagctgca    1740
tttttacaga acagaaatgc aacgcgaaag cgctatttta ccaacgaaga atctgtgctt    1800 cattttgta aaacaaaaat gcaacgcgag agcgctaatt tttcaaacaa agaatctgag     1860
ctgcattttt acagaacaga aatgcaacgc gagagcgcta ttttaccaac aaagaatcta    1920
tacttctttt ttgttctaca aaaatgcatc ccgagagcgc tattttttcta acaaagcatc   1980 ttagattact ttttttctcc tttgtgcgct ctataatgca gtctcttgat aactttttgc    2040
actgtaggtc cgttaaggtt agaagaaggc tactttggtg tctattttct cttccataaa    2100
aaaagcctga ctccacttcc cgcgttact gattactagc gaagctgcgg gtgcattttt     2160
tcaagataaa ggcatccccg attatattct ataccgatgt ggattgcgca ctttgtga     2220 acagaaagtg atagcgttga tgattcttca ttggtcagaa aattatgaac ggtttcttct    2280
attttgtctc tatatactac gtataggaaa tgtttacatt ttcgtattgt tttcgattca    2340
ctctatgaat agttcttact acaattttt tgtctaaaga gtaatactag agataaacat     2400
aaaaaatgta gaggtcgagt ttagatgcaa gttcaaggag cgaaaggtgg atgggtaggt    2460
tatatgggga tatagcacag agatatatag caaagagata cttttgagca atgtttgtgg    2520
aagcggtatt cgcaatattt tagtagctcg ttacagtccg gtgcgttttt ggttttttga    2580
aagtgcgtct tcagagcgct tttggttttc aaaagcgctc tgaagttcct atactttcta    2640
gctagagaat aggaacttcg gaataggaac ttcaaagcgt ttccgaaaac gagcgcttcc    2700
gaaaatgcaa cgcgagctgc gcacatacag ctcactgttc acgtcgcacc tatatctgcg    2760
tgttgcctgt atatatatat acatgagaag aacggcatag tgcgtgttta tgcttaaatg    2820
cgttatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgataa    3060
taatggtttc ttaggggggat ctgtttagct tgcctcgtcc ccgccgggtc acccggccag   3120
cgacatggag gcccagaata ccctccttga cagtcttgac gtgcgcagct caggggcatg    3180
atgtgactgt cgcccgtaca tttagcccat acatccccat gtataatcat ttgcatccat    3240
acattttgat ggccgcacgg cgcgaagcaa aaattacggc tcctcgctgc agacctgcga    3300
gcagggaaac gctcccctca cagacgcgtt gaattgtccc cacgccgcgc ccctgtagag    3360
aaatataaaa ggttaggatt tgccactgag gttcttcttt catatacttc cttttaaat    3420 cttgctagga tacagttctc acatcacatc cgaacataaa caaccatggg taaggaaaag    3480
actcacgttt cgaggccgcg attaaattcc aacatggatg ctgatttata tgggtataaa    3540
tgggctcgcg ataatgtcgg gcaatcaggt gcgacaatct atcgattgta tgggaagccc    3600
gatgcgccag agttgtttct gaaacatggc aaaggtagcg ttgccaatga tgttacagat    3660
gagatggtca gactaaactg gctgacggaa tttatgcctc ttccgaccat caagcatttt    3720
atccgtactc ctgatgatgc atggttactc accactgcga tccccggcaa acagcattc     3780 caggtattag aagaatatcc tgattcaggt gaaaatattg ttgatgcgct ggcagtgttc    3840
```

```
ctgcgccggt tgcattcgat tcctgtttgt aattgtcctt ttaacagcga tcgcgtatttt    3900 cgtctcgctc aggcgcaatc acgaatgaat aacggtttgg ttgatgcgag tgattttgat    3960
gacgagcgta atggctggcc tgttgaacaa gtctggaaag aaatgcataa gcttttgcca    4020
ttctcaccgg attcagtcgt cactcatggt gatttctcac ttgataacct tatttttgac    4080
gaggggaaat aataggttg tattgatgtt ggacgagtcg gaatcgcaga ccgataccag     4140
gatcttgcca tcctatggaa ctgcctcggt gagttttctc cttcattaca gaaacggctt    4200
tttcaaaaat atggtattga taatcctgat atgaataaat tgcagtttca tttgatgctc    4260
gatgagtttt tctaatcagt cctcggagat ccgtccccct tttcctttgt cgatatcatg    4320
taattagtta tgtcacgctt acattcacgc cctcccccca catccgctct aaccgaaaag    4380
gaaggagtta gacaacctga agtctaggtc cctatttatt tttttatagt tatgttagta    4440
ttaagaacgt tatttatatt tcaaattttt cttttttttc tgtacagacg cgtgtacgca    4500
tgtaacatta tactgaaaac cttgcttgag aaggttttgg gacgctcgaa ggctttaatt    4560
tgcaagctgg agaccaacat gtgagcaaaa ggccagcaaa aggccaggaa ccgtaaaaag    4620
gccgcgttgc tggcgttttt ccataggctc cgcccccctg acgagcatca caaaaatcga    4680
cgctcaagtc agaggtggcg aaacccgaca ggactataaa gataccaggc gtttccccct    4740
ggaagctccc tcgtgcgctc tcctgttccg accctgccgc ttaccggata cctgtccgcc    4800
tttctccctt cgggaagcgt ggcgctttct caatgctcac gctgtaggta tctcagttcg    4860
gtgtaggtcg ttcgctccaa gctgggctgt gtgcacgaac ccccgttca gcccgaccgc    4920 tgcgccttat ccgtaacta tcgtcttgag tccaacccgg taagacacga cttatcgcca    4980
ctggcagcag ccactggtaa caggattagc agagcgaggt atgtaggcgg tgctacagag    5040
ttcttgaagt ggtggcctaa ctacggctac actagaagga cagtatttgg tatctgcgct    5100
ctgctgaagc cagttacctt cggaaaaaga gttggtagct cttgatccgg caaacaaacc    5160
accgctggta gcggtggttt ttttgtttgc aagcagcaga ttacgcgcag aaaaaaagga    5220
tctcaagaag atcctttgat cttttctacg gggtctgacg ctcagtggaa cgaaaactca    5280
cgttaaggga ttttgg                                                    5296
```

<210> SEQ ID NO 3
<211> LENGTH: 6187
<212> TYPE: DNA
<213> ORGANISM: Artificial Sequence
<220> FEATURE:
<223> OTHER INFORMATION: Synthetic Sequence

<400> SEQUENCE: 3

```
tcatgagggg atcccccaca caccatagct tcaaaatgtt tctactcctt ttttactctt      60
ccagattttc tcggactccg cgcatcgccg taccacttca aaacacccaa gcacagcata     120
ctaaatttcc cctctttctt cctctagggt gtcgttaatt acccgtacta aaggtttgga    180
aaagaaaaaa gagaccgcct cgtttctttt tcttcgtcga aaaggcaat aaaaattttt      240 atcacgtttc ttttcttga aaattttttt tttgattttt ttctcttcg atgacctccc      300 attgatattt aagttaataa acggtcttca atttctcaag tttcagtttc attttcttg     360 ttctattaca acttttttta cttccttgctc attagaaaga aagcatagca atctaatcta    420
agggcggtgt tgacaattaa tcatcggcat agtatatcgg cctaggcttt acactttatg    480
cttccggctc gtataatgtg tggaattgtg agcggataac aatttcacac aggaaacagc    540
gtatgagcac aaaaaagaaa ccattaacac aagagcagct tgaggacgca cgtcgcctta    600
```

```
aagcaattta tgaaaaaaag aaaaatgaac ttggcttatc ccaggaatct gtcgcagaca      660
agatggggat ggggcagtca ggcgttggtg ctttatttaa tggcatcaat gcattaaatg      720
cttataacgc cgcattgctt gcaaaaattc tcaaagttag cgttgaagaa tttagccctt      780
caatcgccag agaaatctac gagatgtatg aagcggttaa tatgcagccg tcacttagaa      840
gtgagtatga gtaccctgtt ttttctcatg ttcaggcagg gatgttctca cctgagctta      900
gaacctttac caaaggtgat gcggagagat gggtaagcac aaccaaaaaa gccagtgatt      960
ctgcattctg gcttgaggtt gaaggtaatt ccatgaccgc accaacaggc tccaagccaa     1020
gctttcctga cggaatgtta attctcgttg accctgagca ggctgttgag ccaggtgatt     1080
tctgcatagc cagacttggg ggtgatgagt ttaccttcaa gaaactgatc agggatagcg     1140
gtcaggtgtt tttacaacca ctaaacccac agtacccaat gatcccatgc aatgagagtt     1200
gttccgttgt ggggaaagtt atcgctagtc agtggcctga agagacgttt ggcgaattca     1260
agcttgagct cagatctcag ctgggcccgg taccgcggcc gctcgagtcg acctgcagcc     1320
aagctaattc cgggcgaatt tcttatgatt tatgattttt attattaaat aagttataaa     1380
aaaaataagt gtatacaaat tttaaagtga ctcttaggtt ttaaaacgaa aattcttgtt     1440
cttgagtaac tctttcctgt aggtcaggtt gctttctcag gtatagcatg aggtcgctct     1500
tattgaccac acctctaccg gcatgccgag caaatgcctg caaatcgctc cccatttcac     1560
ccaattgtag atatgctaac tccagcaatg agttgatgaa tctcggtgtg tattttatgt     1620
cctcagagga caatacctgt tgtaatccgt cccaagctaa cgaagcatct gtgcttcatt     1680
ttgtagaaca aaaatgcaac gcgagagcgc taattttttca aacaaagaat ctgagctgca     1740 ttttttacaga acagaaatgc aacgcgaaag cgctatttta ccaacgaaga atctgtgctt     1800 cattttttgta aaacaaaaat gcaacgcgag agcgctaatt tttcaaacaa agaatctgag     1860 ctgcatttttt acagaacaga aatgcaacgc gagagcgcta ttttaccaac aaagaatcta     1920
tacttctttt ttgttctaca aaaatgcatc ccgagagcgc tatttttcta acaaagcatc     1980
ttagattact ttttttctcc tttgtgcgct ctataatgca gtctcttgat aacttttgc       2040 actgtaggtc cgttaaggtt agaagaaggc tactttggtg tctatttttct cttccataaa     2100 aaaagcctga ctccacttcc cgcgtttact gattactagc gaagctgcgg gtgcatttttt    2160 tcaagataaa ggcatccccg attatattct ataccgatgt ggattgcgca ctttgtga       2220 acagaaagtg atagcgttga tgattcttca ttggtcagaa aattatgaac ggtttcttct     2280 atttttgtctc tatatactac gtataggaaa tgtttacatt ttcgtattgt tttcgattca    2340
ctctatgaat agttcttact acaatttttt tgtctaaaga gtaatactag agataaacat     2400
aaaaaatgta gaggtcgagt ttagatgcaa gttcaaggag cgaaaggtgg atgggtaggt     2460
tatataggga tatagcacag agatatatag caaagagata cttttgagca atgtttgtgg     2520
aagcggtatt cgcaatatttt tagtagctcg ttacagtccg gtgcgttttt ggttttttga    2580
aagtgcgtct tcagagcgct tttggttttc aaaagcgctc tgaagttcct atactttcta    2640
gctagagaat aggaacttcg gaataggaac ttcaaagcgt ttccgaaaac gagcgcttcc     2700
gaaaatgcaa cgcgagctgc gcacatacag ctcactgttc acgtcgcacc tatatctgcg     2760
tgttgcctgt atatatatat acatgagaag aacggcatag tgcgtgttta tgcttaaatg     2820
cgttatggtg cactttgcgc cgaataaata cctgtgacgg aagatcactt cgcagaataa     2880
ataaatcctg gtgtccctgt tgataccggg aagccctggg ccaactttttg gcgaaaatga     2940 gacgttgatc ggcacgtaag aggttccaac tttcaccata atgaaataag atcactaccg     3000
```

```
ggcgtatttt ttgagttatc gagattttca ggagctaagg aagctaaaat ggagaaaaaa    3060
atcactggat ataccaccgt tgatatatcc caatggcatc gtaaagaaca ttttgaggca    3120
tttcagtcag ttgctcaatg tacctataac cagaccgttc agctggatat tacggccttt    3180
ttaaagaccg taaagaaaaa taagcacaag ttttatccgg cctttattca cattcttgcc    3240
cgcctgatga atgctcatcc ggaattccgt atggcaatga agacggtga gctggtgata    3300 tgggatagtg ttcacccttg ttacaccgtt ttccatgagc aaactgaaac gttttcatcg    3360
ctctggagtg aataccacga cgatttccgg cagtttctac acatatattc gcaagatgtg    3420
gcgtgttacg gtgaaaacct ggcctatttc cctaaagggt ttattgagaa tatgtttttc    3480
gtctcagcca atccctgggt gagtttcacc agttttgatt taaacgtggc caatatggac    3540
aacttcttcg cccccgtttt caccatgggc aaatattata cgcaaggcga caaggtgctg    3600
atgccgctgg cgattcaggt tcatcatgcc gtttgtgatg gcttccatgt cggcagaatg    3660
cttaatgaat acaacagta ctgcgatgag tggcagggcg gggcgtaaga cgtctattta    3720
ttcattggcc agcttatata acgtctcctt gaagtacttt atcaaatgtg tgttctcctc    3780
atgggttcca acgtaattc tcaaacatcc ggaacagcct aattcgttac ctctaaatct    3840
gacgacaacc ccagattgag tagccaattg gtagtataac ttctttgcca agacattgtc    3900 accccgttg atccgtatta aaagaaaatt agcatctaat ccaccaacat attggtcatc    3960
aacgtaatcc aaagcagtta attcctttaa gaggcgcatt ttctcttcat tgattatttt    4020
cgaagtggct tccatcttct ttagattact gtcttgaaca gcttttagtg catattcaga    4080
ggctagggag gaaatattat aaggcgcctt cattgcattt aaaattctgg ccaactctgc    4140
tgttgcatat gtcataccca acctaatccc ggctaaaccg aatgacttgg atagagtttg    4200
caaagtaacc aagttaggat acttggtgac tagtggagct gtagagccac cacaaaaatc    4260
tacgtaagct tcatcaacaa cgactaaccc attgtcccaa ttctgtaaga ccttttcgat    4320
taaactggtc ttaattttgg ctcctgttgg attacctggt gaagtaacga acatcaactt    4380
aattagcggg tcgttttca aaatggttaa tacagcttcg gtatccattt gaaaagaacc    4440
gtcggaaaca gttaaaggac attggacgac ttctatatca ttaatgtttg cacaaacaga    4500
atacatagaa tatgttggtg gaagaaccag aatcttttct ttcccgggaa cacagcatgc    4560
tctaataata gcatcaatac tctcatcaga tcccacacct aggcacagat tgtcagcagt    4620
taaaggtttt acctctgggt cattggcata actgcttgtt ttgttcctgt atttcgtcat    4680
tgcggtcttg aactccaatt ggtgaggatc tgggtaacga tgtaaattgg tcttgctcaa    4740
ttcaactgga gtaggtccat gggcgttttc attggcgtct agcaatatac cctcggtgaa    4800
atcatctctt gcacagcgat aaggttccaa gttataaatt tttggtctaa caattctttt    4860
caaatcaaaa accatagtgt aattttaata tatacgacac acacgtcctg ctggtttatc    4920
aggaaacaaa ataagagtag tcaatggaaa aactgttttt acatattaga gggtatatta    4980
aacagaactg tgtgcatcct tttcaagtta tataacgtga gagataaaat atcaagtatg    5040
tcatgtcagg gtaagaaaca tcaattgaag tgagtcaaca gatccaagaa aaaaaagcac    5100
taactacgtc actacaccat gaactattga aaattggtag tttagtcatc tcagattcca    5160
ttcattggaa aaaacaattg attcataaca attaacttcg gattagtcat taattatttc    5220
aatgcttgac tcctttttga atagtatcac ccggatcgtg gtcacatgat caaataaatt    5280
attgcattac caatggcttc tgtattagtt actctccagg aaatgtctca acataaccgg    5340
tcaccatatt tatgataaca attttttaacc atttaccctt tatttttgca aagttatgac    5400
```

-continued

| | |
|---|---|
| ctttggaatg cagcagaaga aaaaaattga tgaagtagtc atcaaacagg tttcggcgaa | 5460 |
| agacagatca tgtgagcaaa aggccagcaa aaggccagga accgtaaaaa ggccgcgttg | 5520 |
| ctggcgtttt tccataggct ccgcccccct gacgagcatc acaaaaatcg acgctcaagt | 5580 |
| cagaggtggc gaaacccgac aggactataa agataccagg cgtttccccc tggaagctcc | 5640 |
| ctcgtgcgct ctcctgttcc gaccctgccg cttaccggat acctgtccgc ctttctccct | 5700 |
| tcgggaagcg tggcgctttc tcaatgctca cgctgtaggt atctcagttc ggtgtaggtc | 5760 |
| gttcgctcca agctgggctg tgtgcacgaa ccccccgttc agcccgaccg ctgcgcctta | 5820 |
| tccggtaact atcgtcttga gtccaacccg gtaagacacg acttatcgcc actggcagca | 5880 |
| gccactggta acaggattag cagagcgagg tatgtaggcg gtgctacaga gttcttgaag | 5940 |
| tggtggccta actacggcta cactagaagg acagtatttg gtatctgcgc tctgctgaag | 6000 |
| ccagttacct tcggaaaaag agttggtagc tcttgatccg gcaaacaaac caccgctggt | 6060 |
| agcggtggtt tttttgtttg caagcagcag attacgcgca gaaaaaaagg atctcaagaa | 6120 |
| gatcctttga tcttttctac ggggtctgac gctcagtgga acgaaaactc acgttaaggg | 6180 |
| attttgg | 6187 |

<210> SEQ ID NO 4
<211> LENGTH: 6187
<212> TYPE: DNA
<213> ORGANISM: Artificial Sequence
<220> FEATURE:
<223> OTHER INFORMATION: Synthetic Sequence

<400> SEQUENCE: 4

| | |
|---|---|
| tcatgagggg atccccccaca caccatagct tcaaaatgtt tctactcctt ttttactctt | 60 |
| ccagattttc tcggactccg cgcatcgccg taccacttca aaacacccaa gcacagcata | 120 |
| ctaaatttcc cctctttctt cctctagggt gtcgttaatt acccgtacta aaggtttgga | 180 |
| aaagaaaaaa gagaccgcct cgtttctttt tcttcgtcga aaaaggcaat aaaaattttt | 240 |
| atcacgtttc ttttcttga aattttttt tttgattttt ttctctttcg atgacctccc | 300 |
| attgatattt aagttaataa acggtcttca atttctcaag tttcagtttc attttttcttg | 360 |
| ttctattaca acttttttta cttcttgctc attagaaaga aagcatagca atctaatcta | 420 |
| agggcggtgt tgacaattaa tcatcggcat agtatatcgg cctaggcttt acactttatg | 480 |
| cttccggctc gtataatgtg tggaattgtg agcggataac aatttcacac aggaaacagc | 540 |
| gtatgagcac aaaaaagaaa ccattaacac aagagcagct tgaggacgca cgtcgcctta | 600 |
| aagcaattta tgaaaaaaag aaaaatgaac ttggcttatc ccaggaatct gtcgcagaca | 660 |
| agatggggat ggggcagtca ggcgttggtg ctttatttaa tggcatcaat gcattaaatg | 720 |
| cttataacgc cgcattgctt gcaaaaattc tcaaagttag cgttgaagaa tttagcccct | 780 |
| caatcgccag agaaatctac gagatgtatg aagcggttag tatgcagccg tcacttagaa | 840 |
| gtgagtatga gtaccctgtt ttttctcatg ttcaggcagg gatgttctca cctgagctta | 900 |
| gaacctttac caaaggtgat gcggagagat gggtaagcac aaccaaaaaa gccagtgatt | 960 |
| ctgcattctg gcttgaggtt gaaggtaatt ccatgaccgc accaacaggc tccaagccaa | 1020 |
| gctttcctga cggaatgtta attctcgttg accctgagca ggctgttgag ccaggtgatt | 1080 |
| tctgcatagc cagacttggg ggtgatgagt ttaccttcaa gaaactgatc agggatagcg | 1140 |
| gtcaggtgtt tttacaacca ctaaacccac agtacccaat gatcccatgc aatgagagtt | 1200 |
| gttccgttgt ggggaaagtt atcgctagtc agtggcctga agagacgttt ggcgaattca | 1260 |

```
agcttgagct cagatctcag ctgggcccgg taccgcggcc gctcgagtcg acctgcagcc    1320
aagctaattc cgggcgaatt tcttatgatt tatgattttt attattaaat aagttataaa    1380
aaaaataagt gtatacaaat tttaaagtga ctcttaggtt ttaaaacgaa aattcttgtt    1440
cttgagtaac tctttcctgt aggtcaggtt gctttctcag gtatagcatg aggtcgctct    1500
tattgaccac acctctaccg gcatgccgag caaatgcctg caaatcgctc cccatttcac    1560
ccaattgtag atatgctaac tccagcaatg agttgatgaa tctcggtgtg tattttatgt    1620
cctcagagga caatacctgt tgtaatccgt cccaagctaa cgaagcatct gtgcttcatt    1680
ttgtagaaca aaaatgcaac gcgagagcgc taatttttca aacaaagaat ctgagctgca    1740
tttttacaga acagaaatgc aacgcgaaag cgctatttta ccaacgaaga atctgtgctt    1800 cattttgta aaacaaaaat gcaacgcgag agcgctaatt tttcaaacaa agaatctgag    1860
ctgcattttt acagaacaga atgcaacgc gagagcgcta ttttaccaac aaagaatcta    1920
tacttctttt ttgttctaca aaaatgcatc ccgagagcgc tattttccta caaagcatc    1980 ttagattact ttttttctcc tttgtgcgct ctataatgca gtctcttgat aacttttgc    2040 actgtaggtc cgttaaggtt agaagaaggc tactttggtg tctatttttct cttccataaa    2100 aaaagcctga ctccacttcc cgcgtttact gattactagc gaagctgcgg gtgcattttt    2160
tcaagataaa ggcatccccg attatattct ataccgatgt ggattgcgca ctttgtga    2220 acagaaagtg atagcgttga tgattcttca ttggtcagaa aattatgaac ggtttcttct    2280
attttgtctc tatatactac gtataggaaa tgtttacatt ttcgtattgt tttcgattca    2340
ctctatgaat agttcttact acaattttttt tgtctaaaga gtaatactag agataaacat    2400 aaaaatgta gaggtcgagt ttagatgcaa gttcaaggag cgaaaggtgg atgggtaggt    2460
tatataggga tatagcacag agatatatag caaagagata cttttgagca atgtttgtgg    2520
aagcggtatt cgcaatattt tagtagctcg ttacagtccg gtgcgttttt ggttttttga    2580
aagtgcgtct tcagagcgct tttggttttc aaaagcgctc tgaagttcct atactttcta    2640
gctagagaat aggaacttcg gaataggaac ttcaaagcgt ttccgaaaac gagcgcttcc    2700
gaaaatgcaa cgcgagctgc gcacatacag ctcactgttc acgtcgcacc tatatctgcg    2760
tgttgcctgt atatatatat acatgagaag aacggcatag tgcgtgttta tgcttaaatg    2820
cgttatggtg cactttgcgc cgaataaata cctgtgacgg aagatcactt cgcagaataa    2880
ataaatcctg gtgtccctgt tgataccggg aagccctggg ccaacttttg gcgaaaatga    2940
gacgttgatc ggcacgtaag aggttccaac tttcaccata atgaaataag atcactaccg    3000
ggcgtatttt ttgagttatc gagattttca ggagctaagg aagctaaaat ggagaaaaaa    3060
atcactggat ataccaccgt tgatatatcc caatggcatc gtaaagaaca ttttgaggca    3120
tttcagtcag ttgctcaatg tacctataac cagaccgttc agctggatat tacggccttt    3180
ttaaagaccg taaagaaaaa taagcacaag ttttatccgg cctttattca cattcttgcc    3240
cgcctgatga atgctcatcc ggaattacgt atggcaatga agacggtga gctggtgata    3300 tgggatagtt tcacccttg ttacaccgtt tccatgagc aaactgaaac gttttcatcg    3360
ctctggagtg aataccacga cgatttccgg cagtttctac acatatattc gcaagatgtg    3420
gcgtgttacg gtgaaaacct ggcctatttc cctaaagggt ttattgagaa tatgttttc    3480 gtctcagcca atccctgggt gagtttcacc agttttgatt taaacgtggc caatatggac    3540
aacttcttcg ccccgttttt caccatgggc aaatattata cgcaaggcga caaggtgctg    3600
atgccgctgg cgattcaggt tcatcatgcc gtttgtgatg gcttccatgt cggcagaatg    3660
```

```
cttaatgaat tacaacagta ctgcgatgag tggcagggcg gggcgtaaga cgtctattta    3720
ttcattggcc agcttatata acgtctcctt gaagtacttt atcaaatgtg tgttctcctc    3780
atgggttcca acggtaattc tcaaacatcc ggaacagcct aattcgttac ctctaaatct    3840
gacgacaacc ccagattgag tagccaattg gtagtataac ttctttgcca agacattgtc    3900 accccgttg atccgtatta aaagaaaatt agcatctaat ccaccaacat attggtcatc    3960
aacgtaatcc aaagcagtta attcctttaa gaggcgcatt ttctcttcat tgattatttt    4020
cgaagtggct tccatcttct ttagattact gtcttgaaca gcttttagtg catattcaga    4080
ggctagggag gaaatattat aaggcgcctt cattgcattt aaaattctgg ccaactctgc    4140
tgttgcatat gtcataccca acctaatccc ggctaaaccg aatgacttgg atagagtttg    4200
caaagtaacc aagttaggat acttggtgac tagtggagct gtagagccac cacaaaaatc    4260
tacgtaagct tcatcaacaa cgactaaccc attgtcccaa ttctgtaaga ccttttcgat    4320
taaactggtc ttaattttgg ctcctgttgg attacctggt gaagtaacga acatcaactt    4380
aattagcggg tcgttttca aaatggttaa tacagcttcg gtatccattt gaaaagaacc    4440
gtcggaaaca gttaaaggac attggacgac ttctatatca ttaatgtttg cacaaacaga    4500
atacatagaa tatgttggtg gaagaaccag aatctttct ttcccgggaa cacagcatgc    4560
tctaataata gcatcaatac tctcatcaga tcccacacct aggcacagat tgtcagcagt    4620
taaaggtttt acctctgggt cattggcata actgcttgtt ttgttcctgt atttcgtcat    4680
tgcggtcttg aactccaatt ggtgaggatc tgggtaacga tgtaaattgg tcttgctcaa    4740
ttcaactgga gtaggtccat gggcgttttc attggcgtct agcaatatac cctcggtgaa    4800
atcatctctt gcacagcgat aaggttccaa gttataaatt tttggtctaa caattctttt    4860
caaatcaaaa accatagtgt aatttttaata tatacgacac acacgtcctg ctggtttatc    4920
aggaaacaaa ataagagtag tcaatggaaa aactgttttt acatattaga gggtatatta    4980
aacagaactg tgtgcatcct tttcaagtta tataacgtga gagataaaat atcaagtatg    5040
tcatgtcagg gtaagaaaca tcaattgaag tgagtcaaca gatccaagaa aaaaaagcac    5100
taactacgtc actacaccat gaactattga aaattggtag tttagtcatc tcagattcca    5160
ttcattggaa aaaacaattg attcataaca attaacttcg gattagtcat taattatttc    5220
aatgcttgac tccttttga atagtatcac ccgatcgtg gtcacatgat caaataaatt    5280
attgcattac caatggcttc tgtattagtt actctccagg aaatgtctca acataaccgg    5340
tcaccatatt tatgataaca atttttaacc atttaccctt tatttttgca agttatgac    5400 ctttggaatg cagcagaaga aaaaaattga tgaagtagtc atcaaacagg tttcggcgaa    5460
agacagatca tgtgagcaaa aggccagcaa aaggccagga accgtaaaaa ggccgcgttg    5520
ctggcgtttt tccataggct ccgcccccct gacgagcatc acaaaaatcg acgctcaagt    5580
cagaggtggc gaaacccgac aggactataa agataccagg cgtttccccc tggaagctcc    5640
ctcgtgcgct ctcctgttcc gaccctgccg cttaccggat acctgtccgc ctttctccct    5700
tcgggaagcg tggcgctttc tcaatgctca cgctgtaggt atctcagttc ggtgtaggtc    5760
gttcgctcca agctgggctg tgtgcacgaa ccccccgttc agcccgaccg ctgcgcctta    5820
tccggtaact atcgtcttga gtccaacccg gtaagacacg acttatcgcc actggcagca    5880
gccactggta acaggattag cagagcgagg tatgtaggcg gtgctacaga gttcttgaag    5940
tggtggccta actacggcta cactagaagg acagtatttg gtatctgcgc tctgctgaag    6000
ccagttacct tcggaaaaag agttggtagc tcttgatccg gcaaacaaac caccgctggt    6060
```

-continued

| | |
|---|---|
| agcggtggtt tttttgtttg caagcagcag attacgcgca gaaaaaaagg atctcaagaa | 6120 |
| gatcctttga tcttttctac ggggtctgac gctcagtgga acgaaaactc acgttaaggg | 6180 |
| attttgg | 6187 |

<210> SEQ ID NO 5
<211> LENGTH: 4320
<212> TYPE: DNA
<213> ORGANISM: Artificial Sequence
<220> FEATURE:
<223> OTHER INFORMATION: Synthetic Sequence

<400> SEQUENCE: 5

| | |
|---|---|
| gaattcgaac ccctcctacg acgtctaaga aaccattatt atcatgacat taacctataa | 60 |
| aaataggcgt atcacgaggc cctttggata accagaagca ataaaaaatc aaatcggatt | 120 |
| tcactatata atctcacttt atctaagatg aatccgatgg aagcatcctg tttctctca | 180 |
| attttttat ctaaaaccca gcgttcgatg cttctttgag cgaacgatca aaataagtg | 240 |
| ccttcccatc aaaaaaatat tgacaacata aaaaactttg tgttatactt gtaacgctac | 300 |
| atggagatta actcaatcta gctagagagg ctttacactt tatgcttccg gctcgtataa | 360 |
| tgtgtggaat tgtgagcgga taacaatttc acacaggaaa cagctatgac catgattacg | 420 |
| gattcactgg aactctagac caaagagagg acacaatgca gggttctgtg acagagtttc | 480 |
| taaaaccgcg cctggttgat atcgagcaag tgagttcgac gcacgccaag gtgacccttg | 540 |
| agcctttaga gcgtggcttt ggccatactc tgggtaacgc actgcgccgt attctgctct | 600 |
| catcgatgcc gggttgcgcg gtgaccgagg ttgagattga tggtgtacta catgagtaca | 660 |
| gcaccaaaga aggcgttcag gaagatatcc tggaaatcct gctcaacctg aaagggctgg | 720 |
| cggtgagagt tcagggcaaa gatgaagtta ttcttacctt gaataaatct ggcattggcc | 780 |
| ctgtgactgc agccgatatc acccacgacg gtgatgtcga atcgtcaag ccgcagcacg | 840 |
| tgatctgcca cctgaccgat gagaacgcgt ctattagcat gcgtatcaaa gttcagcgcg | 900 |
| gtcgtggtta tgtgccggct tctaccgaa ttcattcgga agaagatgag cgcccaatcg | 960 |
| gccgtctgct ggtcgacgca tgctacagcc ctgtggagcg tattgcctac aatgttgaag | 1020 |
| cagcgcgtgt agaacagcgt accgacctgg acaagctggt catcgaaatg gaaaccaacg | 1080 |
| gcacaatcga tcctgaagag gcgattcgtc gtgcggcaac cattctggct gaacaactgg | 1140 |
| aagctttcgt tgacttacgt gatgtacgtc agcctgaagt gaaagaagag aaaccagagg | 1200 |
| cggccgcgca attggagctc ctcgagggat cctaagtaag aagacacagg cgagagccgc | 1260 |
| tagtctagag actagaaaaa ggccgacaag tcccgctccg ctgaagatcc tggcgtaata | 1320 |
| gcgaagaggc ccgcaccgat cgcccttccc aacagttgcg cagcctgaat ggcgaatggg | 1380 |
| acgcgccctg tagcggcgca ttaagcgcgg cgggtgtggt ggttacgcgc agcgtgaccg | 1440 |
| ctacacttgc cagcgcccta gcgcccgctc ctttcgcttt cttcccttcc tttctcgcca | 1500 |
| cgttcgccgg ctttccccgt caagctctaa atcggggggct ccctttaggg ttccgattta | 1560 |
| gtgctttacg gcacctcgac cccaaaaaac ttgattaggg tgatggttca cgtagtgggc | 1620 |
| catcgccctg atagacggtt tttcgccctt tgacgttgga gtccacgttc tttaatagtg | 1680 |
| gactcttgtt ccaaactgga acaacactca accctatctc ggtctattct tttgatttat | 1740 |
| aagggatttt gccgatttcg gcctattggt taaaaaatga gctgatttaa caaaaattta | 1800 |
| acgcgaattt taacaaaata ttaacgctta caatttaggt ggcactttc ggggaaatgt | 1860 |
| gcgcggaacc cctatttgtt tatttttcta aatacattca aatatgtatc cgctcatgag | 1920 |

```
acaataaccc tgataaatgc ttcaataata ttgaaaaagg aagagtatga gtattcaaca    1980
tttccgtgtc gcccttattc ccttttttgc ggcattttgc cttcctgttt ttgctcaccc    2040
agaaacgctg gtgaaagtaa agatgctgaa agatcagttg ggtgcacgag tgggttacat    2100
cgaactggat ctcaacagcg gtaagatcct tgagagtttt cgccccgaag aacgttttcc    2160
aatgatgagc acttttaaag ttctgctatg tggcgcggta ttatcccgtg ttgacgccgg    2220
gcaagagcaa ctcggtcgcc gcatacacta ttctcagaat gacttggttg agtactcacc    2280
agtcacagaa aagcatctta cggatggcat gacagtaaga gaattatgca gtgctgccat    2340
aaccatgagt gataacactg cggccaactt acttctgaca acgatcggag gaccgaagga    2400
gctaaccgct tttttgcaca acatgggggga tcatgtaact cgccttgatc gttgggaacc    2460
ggagctgaat gaagccatac caaacgacga gcgtgacacc acgatgcctg cagcaatggc    2520
aacaacgttg cgcaaactat taactggcga actacttact ctagcttccc ggcaacaatt    2580
aatagactgg atggaggcgg ataaagttgc aggaccactt ctgcgctcgg cccttccggc    2640
tggctggttt attgctgata aatctggagc cggtgagcgt gggtctcgcg gtatcattgc    2700
agcactgggg ccagatggta agccctcccg tatcgtagtt atctacacga cggggagtca    2760
ggcaactatg gatgaacgaa atagacagat cgctgagata ggtgcctcac tgattaagca    2820
ttggtaactg tcagaccaag tttactcata tatactttag attgatttaa aacttcattt    2880
ttaatttaaa aggatctagg tgaagatcct ttttgataat ctcatgacca aaatccctta    2940
acgtgagttt tcgttccact gagcgtcaga ccccgtagaa aagatcaaag gatcttcttg    3000
agatcctttt tttctgcgcg taatctgctg cttgcaaaca aaaaaaccac cgctaccagc    3060 ggtggttttgt ttgccggatc aagagctacc aactctttt ccgaaggtaa ctggcttcag    3120
cagagcgcag ataccaaata ctgtccttct agtgtagccg tagttaggcc accacttcaa    3180
gaactctgta gcaccgccta catacctcgc tctgctaatc ctgttaccag tggctgctgc    3240
cagtggcgat aagtcgtgtc ttaccgggtt ggactcaaga cgatagttac cggataaggc    3300
gcagcggtcg gctgaacgg gggggttcgtg cacacagccc agcttggagc gaacgaccta    3360
caccgaactg agatacctac agcgtgagct atgagaaagc gccacgcttc ccgaagggag    3420
aaaggcggac aggtatccgg taagcggcag ggtcggaaca ggagagcgca cgagggagct    3480 tccagggga aacgcctggt atctttatag tcctgtcggg tttcgccacc tctgacttga    3540
gcgtcgattt ttgtgatgct cgtcaggggg gcggagccta tggaaaaacg ccagcaacgc    3600 ggcctttta cggttcctgg ccttttgctg gccttttgct cacatgttct ttcctgcgtt    3660
atcccctgat tctgtggata accgtattac cgcctttgag tgagctgata ccgctcgccg    3720
cagccgaacg accgagcgca gcgagtcagt gagcgaggaa gcggaagagc gcctgatgcg    3780
gtattttctc cttacgcatc tgtgcggtat ttcacaccgc atatggtgca ctctcagtac    3840
aatctgctct gatgccgcat agttaagcca gtatacactc cgctatcgct acgtgactgg    3900
gtcatggctg cgccccgaca cccgccaaca cccgctgacg cgccctgacg ggcttgtctg    3960
ctcccggcat ccgcttacag acaagctgtg accgtctccg ggagctgcat gtgtcagagg    4020
ttttcaccgt catcaccgaa acgcgcgagg cagctgcggt aaagctcatc agcgtggtcg    4080
tgaagcgatt cacagatgtc tgcctgttca tccgcgtcca gctcgttgag tttctccaga    4140
agcgttaatg tctggcttct gataaagcgg gccatgttaa gggcggtttt ttcctgtttg    4200
gtcactgatg cctccgtgta agggggattt ctgttcatgg gggtaatgat accgatgaaa    4260
cgagagagga tgctcacgat acgggttact gatgatgaac atgcccggtt actggaacgg    4320
```